United States Patent
Green et al.

(10) Patent No.: US 8,716,316 B2
(45) Date of Patent: May 6, 2014

(54) POSITIVE ALLOSTERIC MODULATORS (PAM)

(71) Applicant: Hoffmann-La Roche Inc., Nutley, NJ (US)

(72) Inventors: Luke Green, Basel (CH); Wolfgang Guba, Muellheim (DE); Georg Jaeschke, Basel (CH); Synese Jolidon, Blauen (CH); Lothar Lindemann, Basel (CH); Antonio Ricci, Birsfelden (CH); Daniel Rueher, Raedersdorf (FR); Heinz Stadler, Basel (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/741,404

(22) Filed: Jan. 15, 2013

(65) Prior Publication Data

US 2013/0131056 A1    May 23, 2013

Related U.S. Application Data

(63) Continuation-in-part of application No. 12/908,014, filed on Oct. 20, 2010, now Pat. No. 8,389,536.

(30) Foreign Application Priority Data

Oct. 27, 2009    (EP) ..................... 09174136

(51) Int. Cl.
   *A61K 31/4427*    (2006.01)
(52) U.S. Cl.
   USPC ....................... 514/336; 546/268.1
(58) Field of Classification Search
   USPC ...................... 546/268.1
   See application file for complete search history.

(56) References Cited

U.S. PATENT DOCUMENTS

2009/0042855 A1    2/2009    Conn et al.

FOREIGN PATENT DOCUMENTS

| EP | 1958666 | 8/2008 |
|---|---|---|
| WO | 02/068409 | 9/2002 |
| WO | 2005/044797 | 5/2005 |
| WO | 2006/005608 | 1/2006 |
| WO | 2006/048771 | 5/2006 |
| WO | 2006/129199 | 12/2006 |
| WO | 2008/151184 | 12/2008 |
| WO | 2009/098208 | 8/2009 |

OTHER PUBLICATIONS

De Paulis et al., Journal of Medicinal Chemistry 49(11):3332-3344 (2006).
Mutel, V., Expert Opinion Therapeutic Patents 12(12):1845-1852 (2003).
Wu et al., Molecular Pharmacology 40:333-336 (1991).
(International Search Report for PCT/EP2010/066016 Mar. 10, 2011).
Kinney et al., Journal of Pharma & Experimental Ther. 313(1):199-206 (2005).

*Primary Examiner* — Brian McDowell

(57) ABSTRACT

The present invention relates to phenylethynyl compounds of formula I

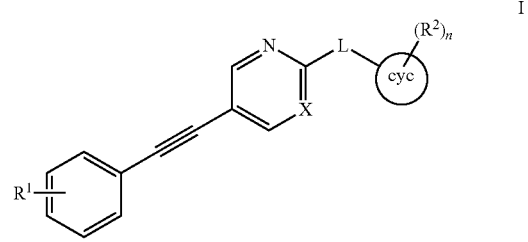

wherein
$R^1$, $R^2$, X, L, $R^3$, $R^4$, $R^{4'}$, cyc, and n are as defined in the specification and claims and to a pharmaceutically acceptable acid addition salt, to a racemic mixture, or to its corresponding enantiomer and/or optical isomer and/or stereoisomer thereof. Compounds of formula I are positive allosteric modulators (PAM) of the metabotropic glutamate receptor subtype 5 (mGluR5). They are useful for the treatment of schizophrenia or cognitive diseases.

14 Claims, No Drawings

POSITIVE ALLOSTERIC MODULATORS (PAM)

PRIORITY TO RELATED APPLICATION(S)

This application is a divisional of U.S. patent application Ser. No. 12/908,014 filed Oct. 20, 2010, now pending; which claims the benefit of European Patent Application No. 09174136.3, filed Oct. 27, 2009, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to site different from the highly conserved orthosteric binding site. Positive allosteric modulators of mGluR5 have emerged recently as novel pharmaceutical entities offering this attractive alternative. Positive allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics*, Vol 313, No. 1, 199-206, 2005.

Positive allosteric modulators are compounds that do not directly activate receptors by themselves, but markedly potentiate agonist-stimulated responses, increase potency and maximum of efficacy. The binding of these compounds increase the affinity of a glutamate-site agonist at its extracellular N-terminal binding site. Positive allosteric modulation is thus an attractive mechanism for enhancing appropriate physiological receptor activation. There is a scarcity of selective positive allosteric modulators for the mGluR5 receptor. Conventional mGluR5 receptor modulators typically lack satisfactory aqueous solubility and exhibit poor oral bioavailability. Therefore, there remains a need for compounds that overcome these deficiencies and that effectively provide selective positive allosteric modulators for the mGluR5 receptor.

SUMMARY OF THE INVENTION

The present invention provides phenylethynyl compounds of formula I

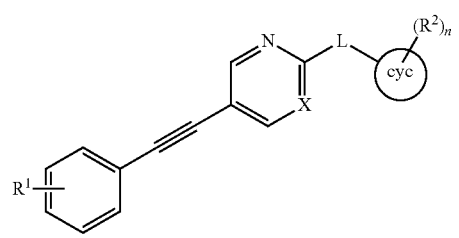

wherein
$R^1$ is hydrogen, halogen, lower alkyl or lower alkyl substituted by halogen;
$R^2$ is hydrogen, lower alkyl, =O, lower alkoxy, phenyl, hydroxy or lower alkyl substituted by hydroxy;
X is N, CF or CH;
L is —$NR^3$—, —$NHC(R^3)_2$—, —O—, —$OC(R^3)_2$—, or —$CR^4R^{4'}$—;
$R^3$ is hydrogen or lower alkyl;
$R^4$ and $R^{4'}$ are each independently hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, corresponding enantiomer, optical isomer and/or stereoisomer thereof.

The present invention provides compounds of formula I and to their pharmaceutically acceptable salts per se. The invention also provides pharmaceutical compositions containing a compound of formula I and a pharmaceutically acceptable carrier. The invention provides processes for the preparation of the compounds and compositions of the invention.

Compounds of formula I are positive allosteric modulators (PAM) of the metabotropic glutamate receptor subtype 5 (mGluR5). They can be used in the treatment or prevention of disorders, relating to positive allosteric modulators for the mGluR5 receptor. In particular, the invention provides methods for the treatment or prevention of disorders, relating to positive allosteric modulators for the mGluR5 receptor, such as schizophrenia, tuberous sclerosis, and cognition and to pharmaceutical compositions containing the compounds of formula I. The most preferred indications for compounds which are positive allosteric modulators are schizophrenia and cognition.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "ethynyl" denotes the group —C≡C—.

The term "lower alkyl substituted by halogen" denotes a lower alkyl groups as defined above, wherein at least one hydrogen atom is replaced by halogen.

The term "lower alkyl substituted by hydroxy" denotes a lower alkyl group as defined above wherein at least one of the hydrogen atoms of the alkyl group is replaced by OH. Examples are hydroxymethyl or hydroxyethyl, in particular hydroxymethyl.

The term cycloalkyl denotes a saturated carbon ring, containing from 3 to 7 carbon ring atoms, for example cyclopropyl, cyclobutyl, cyclopentyl, cyclohexyl or cycloheptyl.

The term heterocycloalkyl denotes a saturated 4, 5 or 6 membered having one or more heteroatom, selected from N, O and S, preferred heteroatoms are N and O. Examples for such rings are tetrahydropyran-2, 3 or 4-yl, oxetan-3-yl, oxazolidinyl, pyrrolidinyl, 1,3-oxazinanyl, tetrahydropyrimidinyl, imidazolidinyl, pyrazolidinyl, piperidinyl, piperazinyl or morpholinyl. If at least one ring atom is N, then heterocyclyl groups having the following formula are preferred:

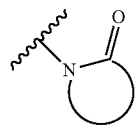 [SMILES: *NC=O]

selected from the group consisting of morpholin-3-one, oxazolidin-2-one, pyrrolidine-2-one, piperidin-2-one, [1,3] oxazinan-2-one, imidazolin-2-one and pyrimidin-2-one;

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

An embodiment of the invention are compounds of formula IA,

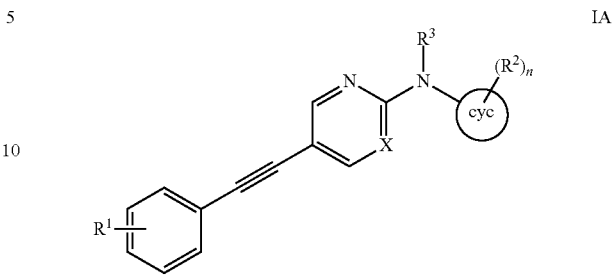

wherein $R^1$ is hydrogen, halogen, lower alkyl or lower alkyl substituted by halogen;

$R^2$ is hydrogen, lower alkyl, =O, lower alkoxy, phenyl, hydroxy or lower alkyl substituted by hydroxy;

X is N, CF or CH;

$R^3$ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, a racemic mixture, corresponding enantiomer, optical isomer, and/or stereoisomer thereof.

A further embodiment of the invention are compounds of formula IA-1,

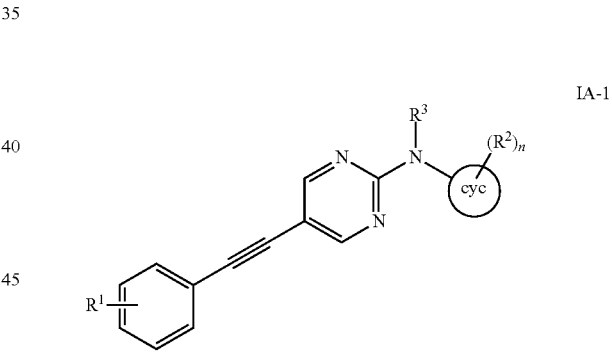

wherein $R^1$ is hydrogen, halogen, lower alkyl or lower alkyl substituted by halogen;

$R^2$ is hydrogen, lower alkyl, =O, lower alkoxy, phenyl, hydroxy or lower alkyl substituted by hydroxy;

$R^3$ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

An embodiment of the invention are further compounds of formula IA-2,

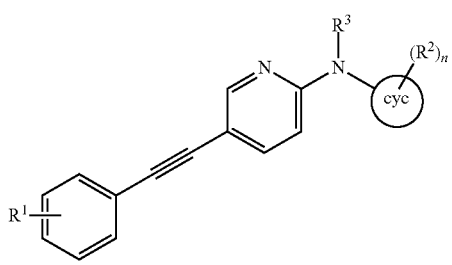

IA-2

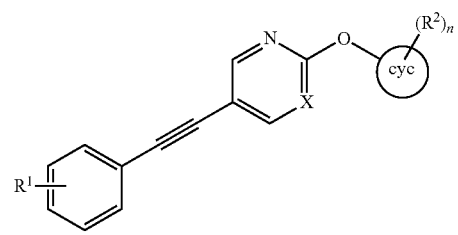

IB wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

R³ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

An embodiment of the invention are further compounds of formula IA-3, wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

X is N, CF or CH;

R³ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

An embodiment of the invention are compounds of formula IC,

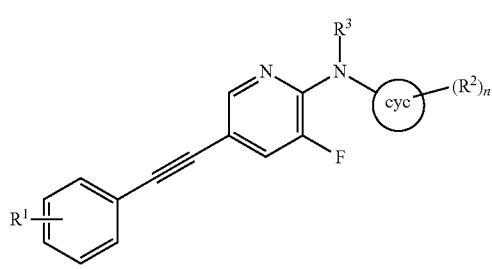

IA-3

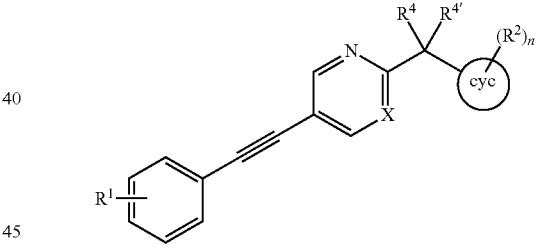

IC wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

R³ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

An embodiment of the invention are compounds of formula IB, wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

X is N, CF or CH;

R⁴ and R⁴' are each independently hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

An embodiment of the invention are compounds of formula ID,

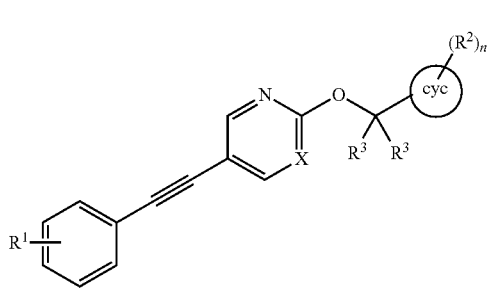

ID

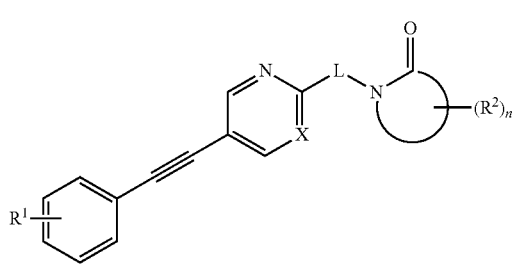

IF wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

X is N, CF or CH;

R³ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

An embodiment of the invention are compounds of formula IE,

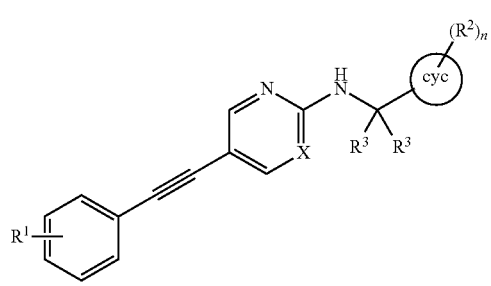

IE wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

X is N, CF or CH;

R³ is hydrogen or lower alkyl;

cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;

or a pharmaceutically acceptable acid addition salt, racemic mixture, corresponding enantiomer, optical isomer, and/or stereoisomer thereof.

A further embodiment of the invention are compounds of formula wherein

R¹ is hydrogen, halogen, lower alkyl or lower alkyl substituted by halogen;

R² is hydrogen, lower alkyl, =O, lower alkoxy, phenyl, hydroxy or lower alkyl substituted by hydroxy;

X is N, CF or CH;

L is —NR³—, —NHC(R³)₂—, —O—, —OC(R³)₂—, or —CR⁴R⁴—;

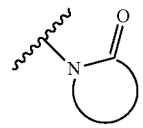

is a 5 or 6 membered heterocycloalkyl, selected from the group consisting of morpholin-3-one, oxazolidin-2-one, pyrrolidin-2-one, piperidin-2-one, [1,3]oxazinan-2-one, imidazolin-2-one and pyrimidin-2-one; and n is 1, 2 or 3;

or a pharmaceutically acceptable acid addition salt, racemic mixture, corresponding enantiomer, optical isomer, and/or stereoisomer thereof.

An embodiment of the invention are compounds of formula IA-1 wherein L is —NR³— and X is N, for example the following compounds:

cyclopentyl-(5-phenylethynyl-pyrimidin-2-yl)-amine;

(5-phenylethynyl-pyrimidin-2-yl)-(tetrahydro-pyran-4-yl)-amine;

rac-(2,2-dimethyl-tetrahydro-pyran-4-yl)-(5-phenylethynyl-pyrimidin-2-yl)-amine;

rac-7-oxa-bicyclo[2.2.1]hept-2-yl-(5-phenylethynyl-pyrimidin-2-yl)-amine;

isomeric mixture of (2,6-dimethoxy-cyclohexyl)-(5-phenylethynyl-pyrimidin-2-yl)-amine;

trans-[4-(5-phenylethynyl-pyrimidin-2-ylamino)-cyclohexyl]-methanol;

trans-4-(5-phenylethynyl-pyrimidin-2-ylamino)-cyclohexanol;

cis and trans mixture of 2-(5-phenylethynyl-pyrimidin-2-ylamino)-cyclohexanol;

cis and trans mixture of 3-(5-phenylethynyl-pyrimidin-2-ylamino)-cyclopentanol;

cis and trans mixture of 2-(5-phenylethynyl-pyrimidin-2-ylamino)-cyclopentanol;

cyclohexyl-(5-phenylethynyl-pyrimidin-2-yl)-amine;

2,2-dimethyl-4-(5-phenylethynyl-pyrimidin-2-ylamino)-cyclohexanol; and (1S,4S or 1R,4R)-2,2-dimethyl-4-(5-phenylethynyl-pyrimidin-2-ylamino)-cyclohexanol.

Further preferred compounds from this group are compounds of formula IA-2 wherein L is —NR³— and X is CH, for example the following compounds:

cyclopentyl-(5-phenylethynyl-pyridin-2-yl)-amine and
(5-phenylethynyl-pyridin-2-yl)-(tetrahydro-pyran-4-yl)-amine.

A further embodiment of the invention are compounds of formula IB, wherein L is —O— and X is N, for example the following compounds
rac-4-(5-phenylethynyl-pyrimidin-2-yloxy)-cyclohexanol;
trans-4-(5-phenylethynyl-pyrimidin-2-yloxy)-cyclohexanol; and
trans-[3-(5-phenylethynyl-pyrimidin-2-yloxy)-cyclobutyl]-methanol.

A further embodiment of the invention are compounds of formula IC, wherein L is —CR⁴R⁴'— and X is CH, for example the following compounds
3-(5-phenylethynyl-pyridin-2-ylmethyl)-oxazolidin-2-one;
1-methyl-3-(5-phenylethynyl-pyridin-2-ylmethyl)-imidazolidin-2-one;
5,5-dimethyl-1-(5-phenylethynyl-pyridin-2-ylmethyl)-pyrrolidin-2-one;
1-phenyl-3-(5-phenylethynyl-pyridin-2-ylmethyl)-imidazolidin-2-one; and
rac-3-[1-(5-phenylethynyl-pyridin-2-yl)-ethyl]-oxazolidin-2-one.

A further embodiment of the invention are compounds of formula IC, wherein L is —CR⁴R⁴' and X is N, for example the following compound
3-(5-phenylethynyl-pyrimidin-2-ylmethyl)-oxazolidin-2-one.

A further embodiment of the invention are compounds of formula ID, wherein L is —OC(R³)₂— and X is N, for example the following compound
2-(3-methyl-oxetan-3-ylmethoxy)-5-phenylethynyl-pyrimidine.

A further embodiment of the invention are compounds of formula IE, wherein L is —NHC(R³)₂— and X is N, for example the following compounds
(3-methyl-oxetan-3-ylmethyl)-(5-phenylethynyl-pyrimidin-2-yl)-amine and
methyl-(5-phenylethynyl-pyrimidin-2-yl)-(tetrahydro-pyran-4-yl)-amine.

A further embodiment of the invention are compounds of formula IE, wherein L is —NHC(R³)₂— and X is CH, for example the following compound
3-(5-phenylethynyl-pyridin-2-ylmethyl)-oxazolidin-2-one.

A further embodiment of the invention are compounds of formula IF, wherein the heterocycloalkyl is

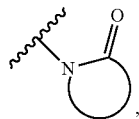

for example the following compounds
4-(5-phenylethynyl-pyridin-2-ylmethyl)-morpholin-3-one;
3-(5-phenylethynyl-pyridin-2-ylmethyl)-oxazolidin-2-one;
1-(5-phenylethynyl-pyridin-2-ylmethyl)-piperidin-2-one;
4,4-dimethyl-1-(5-phenylethynyl-pyridin-2-ylmethyl)-pyrrolidin-2-one;
3-(5-phenylethynyl-pyridin-2-ylmethyl)-[1,3]oxazinan-2-one;
1-methyl-3-(5-phenylethynyl-pyridin-2-ylmethyl)-imidazolidin-2-one;
5,5-dimethyl-1-(5-phenylethynyl-pyridin-2-ylmethyl)-pyrrolidin-2-one;
1-phenyl-3-(5-phenylethynyl-pyridin-2-ylmethyl)-imidazolidin-2-one;
5,5-dimethyl-1-(5-phenylethynyl-pyridin-2-ylmethyl)-piperidin-2-one;
rac-3-methyl-1-(5-phenylethynyl-pyridin-2-ylmethyl)-pyrrolidin-2-one;
1-methyl-3-(5-phenylethynyl-pyridin-2-ylmethyl)-tetrahydro-pyrimidin-2-one;
rac-3-[1-(5-phenylethynyl-pyridin-2-yl)-ethyl]-oxazolidin-2-one; and
3-(5-phenylethynyl-pyrimidin-2-ylmethyl)-oxazolidin-2-one.

An embodiment of the invention are compounds of formula

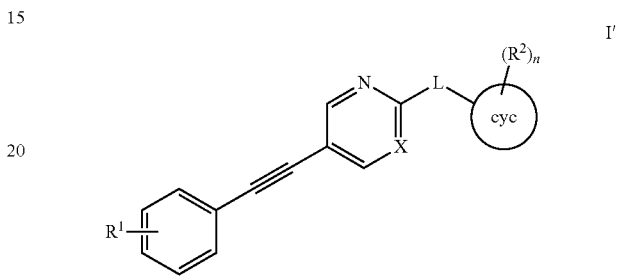

wherein
R¹ is hydrogen, halogen, lower alkyl or lower alkyl substituted by halogen;
R² is hydrogen, halogen, lower alkyl, =O, lower alkyl substituted by halogen, lower alkoxy, lower alkoxy substituted by halogen, S(O)₂-lower alkyl, hydroxy or lower alkyl substituted by hydroxy;
X is N or CH;
L is —NH—, —NHC(R³)₂—, —O—, —CHR⁴— or —S(O₂)—;
R³ is hydrogen or lower alkyl;
R⁴ is hydrogen, hydroxy or lower alkoxy;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, corresponding enantiomer, optical isomer, and/or stereoisomer thereof.

The preparation of compounds of formula I of the present invention can be carried out in sequential or convergent synthetic routes. Syntheses of the compounds of the invention are shown in the following schemes 1 to 8. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variants described below, which process comprises a) reacting a compound of formula

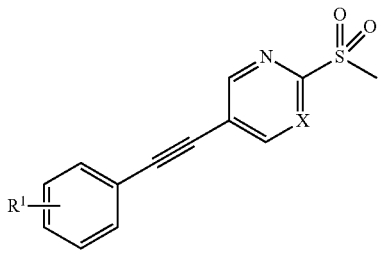

with a suitable amine of formula

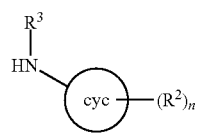

in the presence of a base, selected from triethylamine, and a solvent, selected from THF, to form a compound of formula

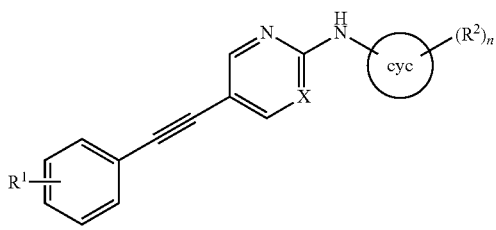

IA wherein the substituents are described above, or
b) reductively aminating a compound of formula

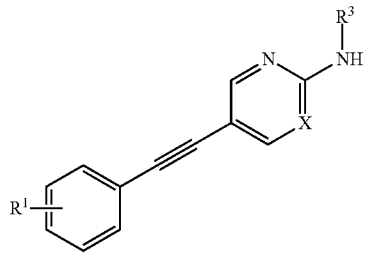

with a compound of formula

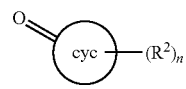

to form a compound of formula

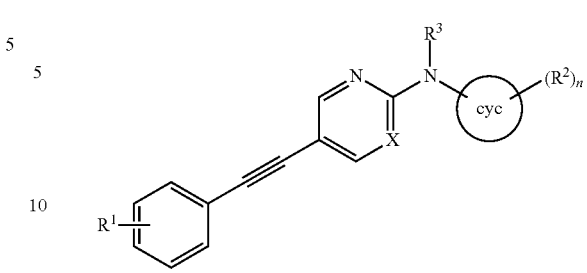

IA wherein the substituents are described above, or
c) a) reacting a compound of formula

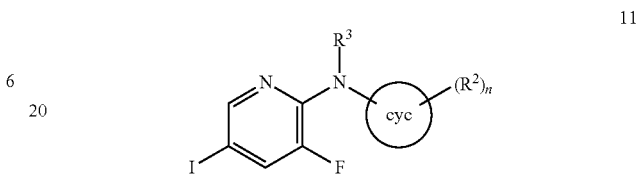

11 with a suitable phenylacetylene compound of formula

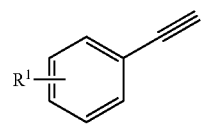

2 in the presence of bis-(tpp)-Pd(II)Cl$_2$, CuI and a base, selected from triethylamine, and a solvent, selected from THF, to form a compound of formula

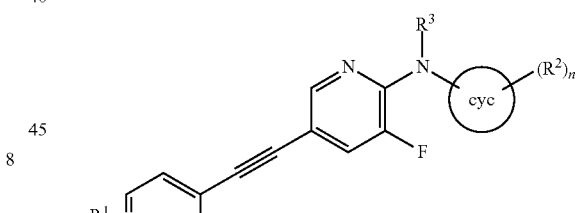

IA-3 wherein the substituents are described above, or
d) a) reacting a compound of formula

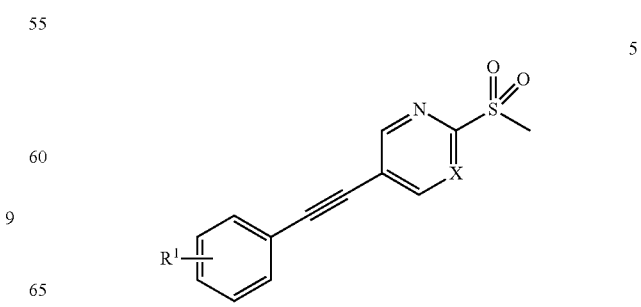

5 with a suitable amine of formula

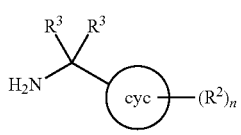   12 in the presence of a base, selected from triethylamine, and a solvent, selected from THF, to form a compound of formula

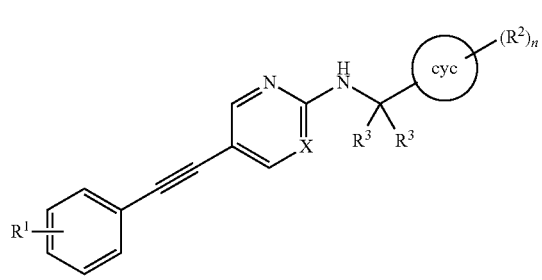   IE wherein the substituents are described above, or e) reacting a compound of formula

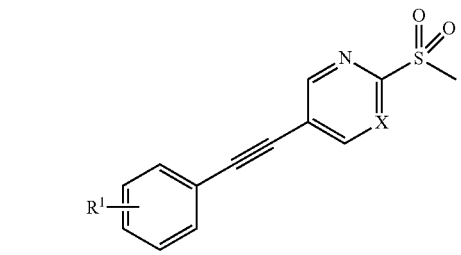   5 with a suitable compound of formula

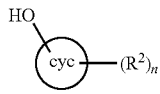   13 in the presence of CsCO₃ and dioxane to form a compound of formula

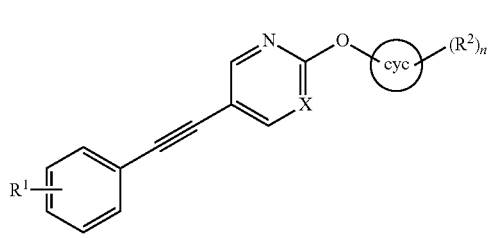   IB wherein the substituents are described above, or f) reacting a compound of formula

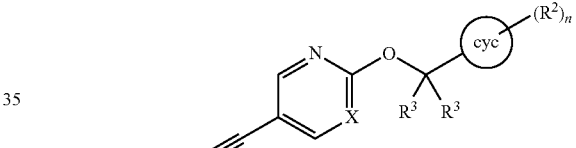   5 with a suitable compound of formula

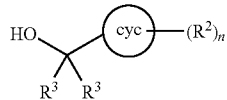   14 in the presence of a base, selected from triethylamine, and a solvent, selected from THF, to form a compound of formula

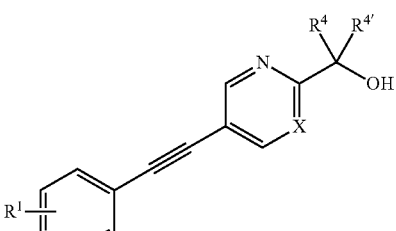   ID wherein the substituents are described above, or g) reacting a compound of formula

16

(Note: image 16 shows compound with R⁴ R⁴′ and OH)

with a suitable compound of formula

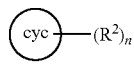   17 in the presence of MeSO₂Cl to form a compound of formula

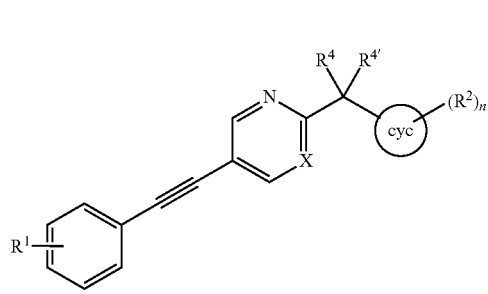

IC wherein the substituents are described above, or if desired, converting the compounds obtained into pharmaceutically acceptable acid addition salts.

The preparation of compounds of formula I is further described in more detail in schemes 1 to 8 and in examples 1-44.

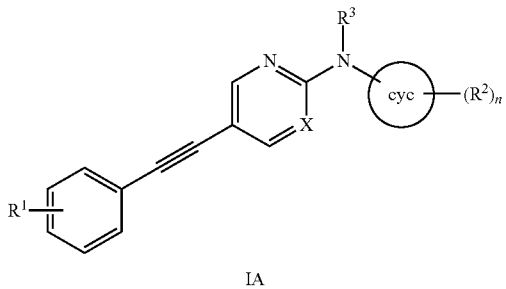

IA

A (5-phenylethynyl-pyrimidin-2-yl)-amine of formula IA can be obtained by Sonogashira coupling of an appropriately substituted phenylacetylene (2) with 5-bromo-2-methylsulfanyl-pyrimidine (3) to yield the corresponding methansulfanyl derivatives (4). Oxidation of the thioether compound with an oxidizing agent such as mCPBA in a solvent like dichloromethane yields the corresponding sulfone derivative (5). Reaction of the sulfone derivative with an appropriately substituted amine (6) in the presence of base such as triethylamine in a solvent like THF yields the desired (5-phenylethynyl-pyrimidin-2-yl)-amine of formula IA.

Scheme 1

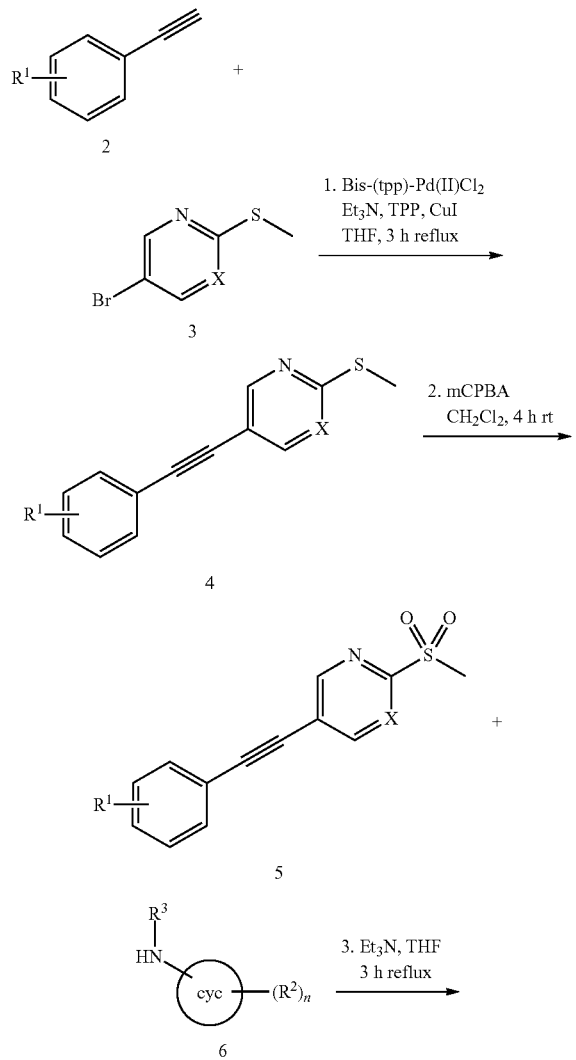

Scheme 2

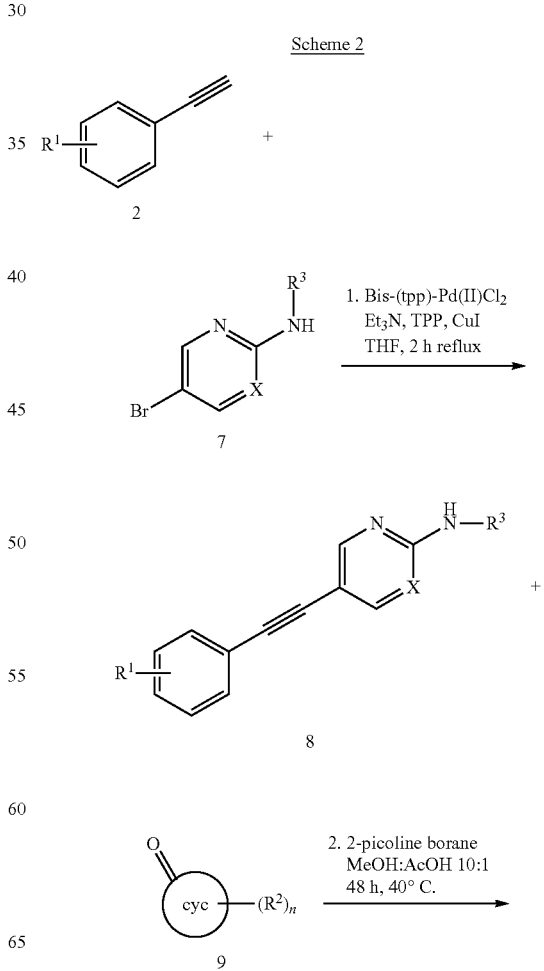

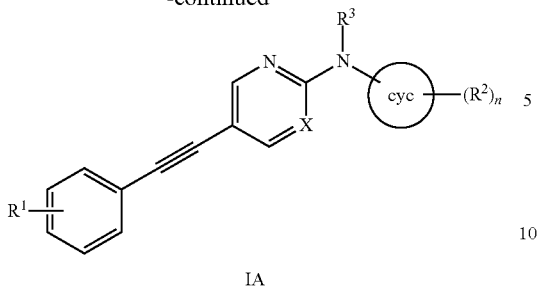

IA

A (5-phenylethynyl-pyridin-2-yl)-amine of formula IA can be obtained by Sonogashira coupling of an appropriately substituted phenylacetylene (2) with an amine (7) to yield the corresponding 5-phenylethynyl-pyridin-2-ylamine derivatives (8). Reductive amination of the 5-phenylethynyl-pyridin-2-ylamine derivatives with an appropriately substituted ketone (9) with a reducing agent such as 2-picoline borane in a solvent mixture like methanol:acetic acid (10:1 v/v) yielded the desired (5-phenylethynyl-pyridin-2-yl)-amines of formula IA.

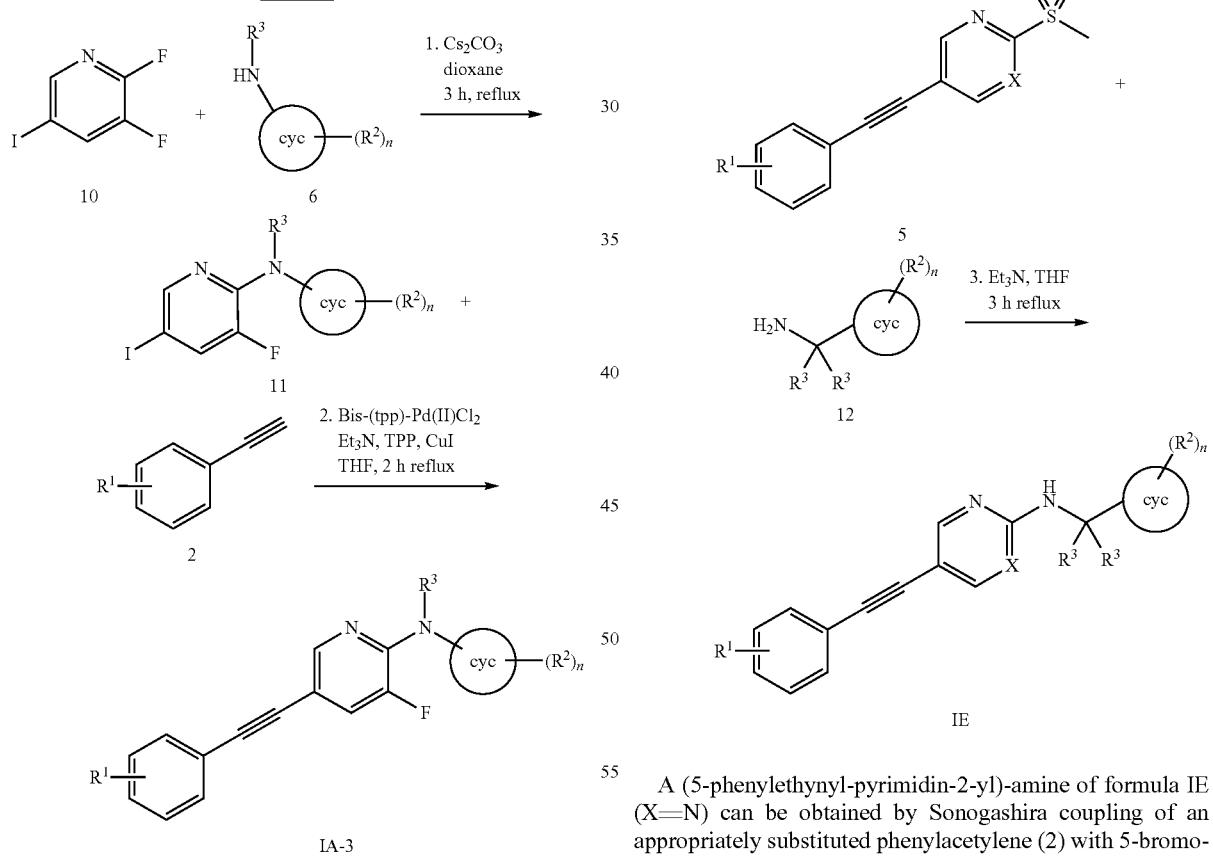

IA-3

A (5-phenylethynyl-3-fluoropyridin-2-yl)-amine of formula IA-3 can be obtained by reacting 2,3-difluoro-5-iodopyridine with an appropriately substituted amine (6) in the presence of a base such as $Cs_2CO_3$ in a solvent like dioxane yielding the desired (5-iodo-3-fluoropyridin-2-yl)-amine (11). Sonogashira coupling with an appropriately substituted phenylacetylene (2) yielded the desired (5-phenylethynyl-3-fluoropyridin-2-yl)-amine of formula IA-3.

Scheme 4

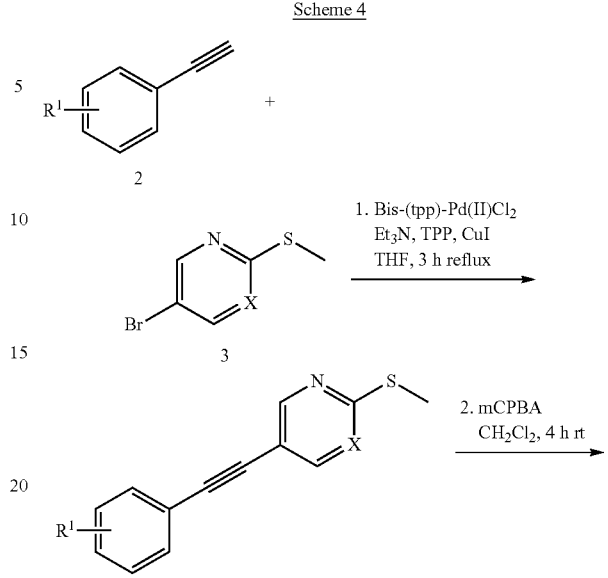

IE

A (5-phenylethynyl-pyrimidin-2-yl)-amine of formula IE (X=N) can be obtained by Sonogashira coupling of an appropriately substituted phenylacetylene (2) with 5-bromo-2-methylsulfanyl-pyrimidine (3) to yield the corresponding methansulfanyl derivatives (4). Oxidation of the thioether compound with an oxidizing agent such as mCPBA in a solvent like dichloromethane yields the corresponding sulfone derivatives (5). Reaction of the sulfone derivatives with an appropriately substituted amine (12) in the presence of base such as triethylamine in a solvent like THF yields the desired (5-phenylethynyl-pyrimidin-2-yl)-amine of formula IE.

Scheme 5

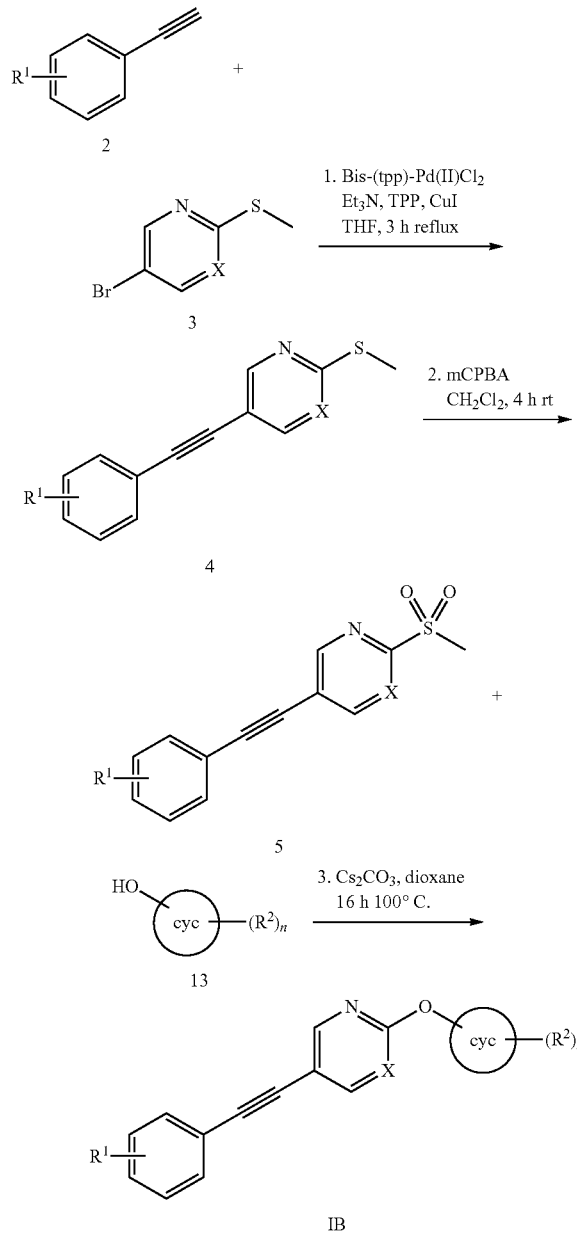

X = N, CH or CF

Scheme 6

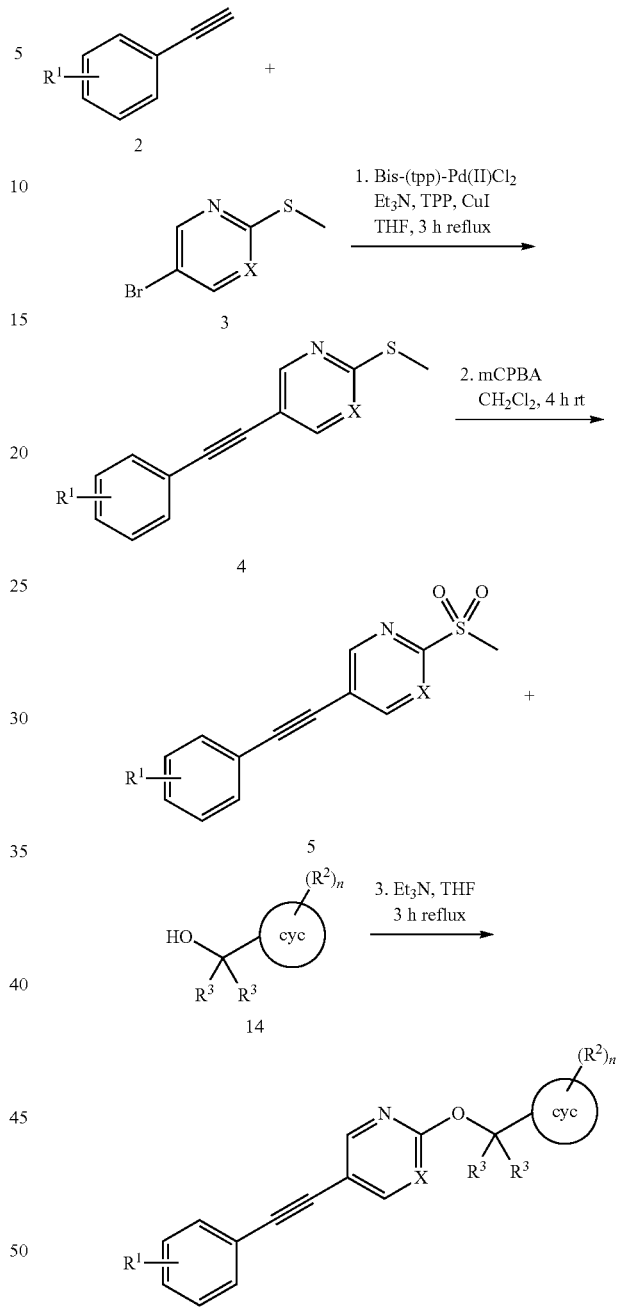

X = N, CH or CF

A (5-phenylethynyl-pyrimidin-2-yloxy)-derivatives or (5-phenylethynyl-pyridin-2-yloxy)-derivatives of formula IB (X=—N= or —CH=) can be obtained by Sonogashira coupling of an appropriately substituted phenylacetylene (2) with 5-bromo-2-methylsulfanyl-pyrimidine or pyridine (3) to yield the corresponding methansulfanyl derivatives (4). Oxidation of the thioether compound with an oxidizing agent such as mCPBA in a solvent like dichloromethane yields the corresponding sulfone derivative (5). Reaction of the sulfone derivatives with an appropriately substituted alcohol (13) in the presence of base such as $Cs_2CO_3$ in a solvent like dioxane yields the desired (5-phenylethynyl-pyrimidin-2-yloxy)-derivatives or (5-phenylethynyl-pyridin-2-yloxy)-derivatives of formula IB.

A (5-phenylethynyl-pyrimidin-2-yloxy)-derivatives or (5-phenylethynyl-pyridin-2-yloxy)-derivatives of formula ID can be obtained by Sonogashira coupling of an appropriately substituted phenylacetylene (2) with 5-bromo-2-methylsulfanyl-pyrimidine or pyridine (3) to yield the corresponding methansulfanyl derivatives (4). Oxidation of the thioether compound with an oxidizing agent such as mCPBA in a solvent like dichloromethane yields the corresponding sulfone derivatives (5). Reaction of the sulfone derivatives with an appropriately substituted alcohol (14) in the presence of base such as $Cs_2CO_3$ in a solvent like dioxane yields the desired (5-phenylethynyl-pyrimidin-2-yloxy)-derivatives or (5-phenylethynyl-pyridin-2-yloxy)-derivatives of formula ID.

Scheme 7

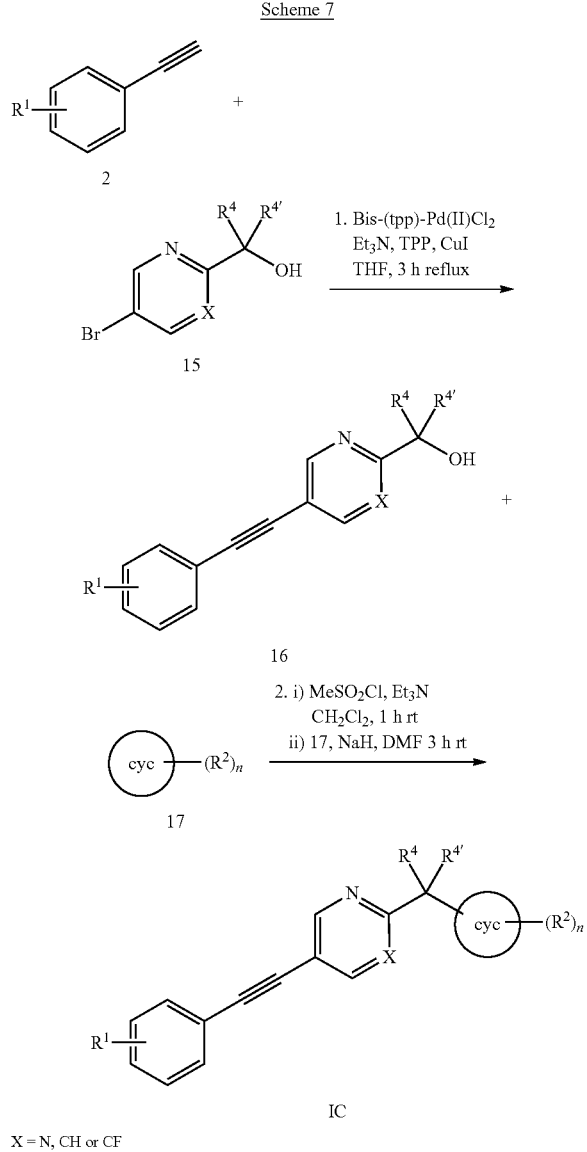

X = N, CH or CF

A (5-phenylethynyl-pyridin-2-yl)-alcohol derivatives or (5-phenylethynyl-pyrimidin-2-yl)-alcohol derivatives of formula IC can be obtained by Sonogashira coupling of an appropriately substituted phenylacetylene (2) with a corresponding 5-bromo-2-pyridin-2-yl)-alcohol or 5-bromo-2-pyrimidin-2-yl)-alcohol (15) to yield the corresponding alcohol derivatives (16). Reaction of the alcohol (16) to the corresponding methanesulfonyl ester with methanesulfonyl chloride in the presence of a base such as triethylamine in a solvent like dichloromethane; followed by coupling with an appropriately substituted lactam, heterocyclic urea or heterocyclic carbamate (17) which has been deprotonated with sodium hydride in a solvent like DMF; yields the desired (5-phenylethynyl-pyridin-2-yl)-alcohol derivatives or (5-phenylethynyl-pyrimidine-2-yl)-alcohol derivatives of formula IC.

Scheme 8

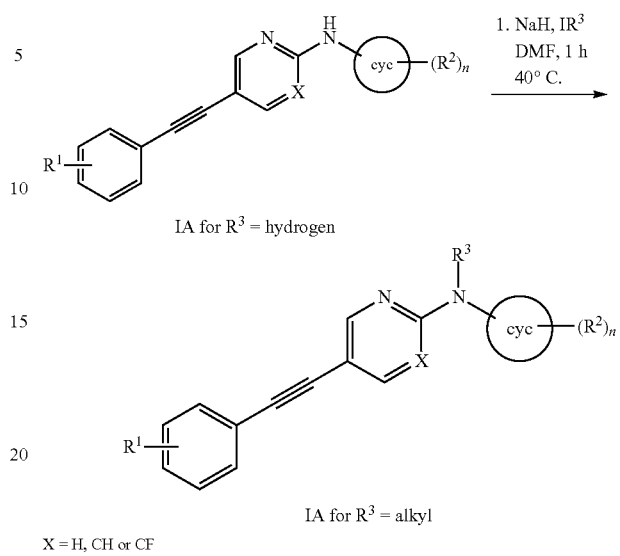

X = H, CH or CF

A tertiary (5-phenylethynyl-pyridin-2-yl)-amine or (5-phenylethynyl-pyrimidin-2-yl)-amine of formula IA Where R3 is lower alkyl can be obtained by deprotonation of and an appropriately substituted secondary amine (IA) with a strong base such as sodium hydride in a solvent like DMF followed by alkylation with a corresponding alkyl halogenide to yield the desired tertiary (5-phenylethynyl-pyridin-2-yl)-amine or (5-phenylethynyl-pyrimidin-2-yl)-amine of formula IA.

Preferably, the compound of formula I as described herein as well as its pharmaceutically acceptable salt is used in the treatment or prevention of psychosis, epilepsy, schizophrenia, Alzheimer's disease, cognitive disorders and memory deficits, chronic and acute pain, restricted brain function caused by bypass operations or transplants, poor blood supply to the brain, spinal cord injuries, head injuries, hypoxia caused by pregnancy, cardiac arrest and hypoglycaemia, ischemia, Huntington's chorea, amyotrophic lateral sclerosis (ALS), dementia caused by AIDS, eye injuries, retinopathy, idiopathic parkinsonism or parkinsonism caused by medicaments, muscle spasms, convulsions, migraine, urinary incontinence, gastrointestinal reflux disorder, liver damage or failure whether drug or disease induced, Fragile-X syndrom, Down syndrom, autism, nicotine addiction, opiate addiction, anxiety, vomiting, dyskinesia, eating disorders, in particular bulimia or anorexia nervosa, and depressions, particularly for the treatment and prevention of acute and/or chronic neurological disorders, anxiety, the treatment of chronic and acute pain, urinary incontinence and obesity.

The preferred indications are schizophrenia and cognitive disorders.

Present invention further relates to the use of a compound of formula I as described herein, as well as its pharmaceutically acceptable salt, for the manufacture of a medicament, preferably for the treatment and prevention of the above-mentioned disorders.

Biological Assay and Data

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the table below are shown the corresponding results for representative compounds with $EC_{50} < 1000$ nM.

| Example | $EC_{50}$ (nM) mGluR5 PAM | Efficacy (%) |
|---|---|---|
| 1 | 26 | 40 |
| 2 | 65 | 46 |
| 3 | 172 | 89 |
| 4 | 195 | 113 |
| 5 | 345 | 105 |
| 6 | 844 | 147 |
| 7 | 179 | 100 |
| 10 | 340 | 72 |
| 11 | 322 | 78 |
| 12 | 560 | 80 |
| 13 | 43 | 43 |
| 14 | 110 | 59 |
| 15 | 52 | 112 |
| 16 | 324 | 113 |
| 17 | 94 | 93 |
| 18 | 192 | 116 |
| 19 | 75 | 55 |
| 20 | 206 | 80 |
| 21 | 78 | 45 |
| 22 | 168 | 121 |
| 23 | 110 | 94 |
| 24 | 101 | 88 |
| 25 | 291 | 133 |
| 26 | 99 | 117 |
| 27 | 200 | 90 |
| 28 | 45 | 61 |
| 29 | 135 | 71 |
| 30 | 83 | 121 |
| 31 | 56 | 122 |
| 32 | 268 | 145 |
| 33 | 132 | 177 |
| 34 | 174 | 119 |
| 35 | 68 | 119 |
| 36 | 84 | 82 |
| 37 | 103 | 84 |
| 38 | 161 | 94 |
| 39 | 93 | 120 |
| 40 | 140 | 123 |
| 41 | 94 | 59 |
| 42 | 631 | 120 |
| 43 | 195 | 84 |
| 44 | 338 | 103 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

As further mentioned earlier, the use of the compounds of formula (I) for the preparation of medicaments useful in the prevention and/or the treatment of the above recited diseases is also an object of the present invention.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions
Comprising Compounds of the Invention Example I Tablets of the following composition are produced in a conventional manner

|  | mg/Tablet |
| --- | --- |
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Experimental Section

Example 1

Cyclopentyl-(5-phenylethynyl-pyrimidin-2-yl)-amine

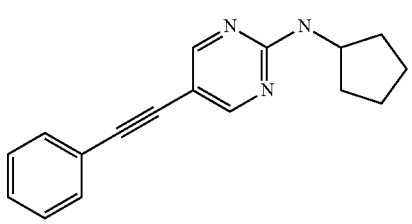

Step 1:
2-Methylsulfanyl-5-phenylethynyl-pyrimidine

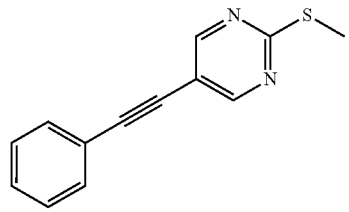 [SMILES: CSc1ncc(C#Cc2ccccc2)cn1]

Bis-(triphenylphosphine)-palladium(II)dichloride (120 mg, 0.16 mmol) were dissolved in 50 ml THF and 5-bromo-2-methylsulfanyl-pyrimidine (840 mg, 4.1 mmol) and phenylacetylene (410 µl, 4.1 mmol) were added at room temperature. Triethylamine (1.36 ml, 12.3 mmol), triphenylphosphine (28 mg, 0.12 mmol) and copper(I)iodide (19 mg, 0.08 mmol) were added and the mixture was stirred for 3 hours at 65° C. The reaction mixture was cooled and extracted once with saturated NaHCO$_3$ solution and three times with ethyl acetate. The organic layers were combined, dried with sodium sulfate, filtered and evaporated to dryness. The crude product was purified by flash chromatography on silicagel (heptane:ethyl acetate 100:0→50:50). The desired compound was obtained as a light yellow solid (400 mg, 44%), MS: m/e=227.3 (M+H$^+$).

Step 2:
2-Methanesulfonyl-5-phenylethynyl-pyrimidine

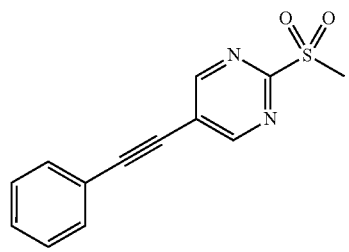 [SMILES: CS(=O)(=O)c1ncc(C#Cc2ccccc2)cn1]

2-Methylsulfanyl-5-phenylethynyl-pyrimidine (360 mg, 1.60 mmol) was dissolved in 20 ml of dichloromethane and 3-chloroperbenzoic acid (870 mg, 3.50 mmol) was added in several portions at 0-5° C. The reaction mixture was stirred for 4 hours at room temperature. Saturated NaHCO$_3$ solution was added and the mixture was extracted three times with ethyl acetate. The organic extracts were dried with sodium sulfate, filtered and evaporated. The crude product was purified by flash chromatography on silicagel (dichloromethane). The desired compound was obtained as a white solid (400 mg, 97%), MS: m/e=259.2 (M+H$^+$).

Step 3:
Cyclopentyl-(5-phenylethynyl-pyrimidin-2-yl)-amine

2-Methanesulfonyl-5-phenylethynyl-pyrimidine (100 mg, 3.11 mmol), cyclopentylamine (80 µl, 6.22 mmol) and Et$_3$N (110 µl, 6.22 mmol) were suspended in 1 ml THF and stirred for 1 hour at 65° C. The reaction mixture was concentrated in vacuo and the residue was purified by flash chromatography by directly loading the crude material onto a silica gel column and eluting with (heptane:ethyl acetate 100:0→0:100). The desired compound was obtained as a white solid (85 mg, 83%), MS: m/e=264.2 (M+H⁺).

Example 2

(5-Phenylethynyl-pyrimidin-2-yl)-(tetrahydro-pyran-4-yl)-amine

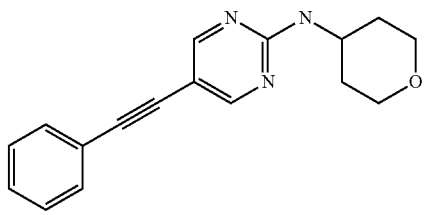 [SMILES: C(#Cc1cnc(NC2CCOCC2)nc1)c1ccccc1]

The title compound, MS: m/e=280.3 (M+H⁺), can be prepared in accordance with the general method of example 1, step 3 from 2-methanesulfonyl-5-phenylethynyl-pyrimidine (example 1, step 2) and tetrahydro-pyran-4-ylamine Example 3 rac-(2,2-Dimethyl-tetrahydro-pyran-4-yl)-(5-phenylethynyl-pyrimidin-2-yl)-amine

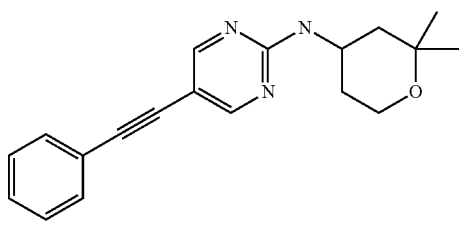 [SMILES: CC1(C)CC(Nc2ncc(C#Cc3ccccc3)cn2)CCO1]

The title compound, MS: m/e=308.2 (M+H⁺), can be prepared in accordance with the general method of example 1, step 3 from 2-methanesulfonyl-5-phenylethynyl-pyrimidine (example 1, step 2) and rac-2,2-dimethyl-tetrahydro-pyran-4-ylamine.

Example 4 rac-7-Oxa-bicyclo[2.2.1]hept-2-yl-(5-phenylethynyl-pyrimidin-2-yl)-amine

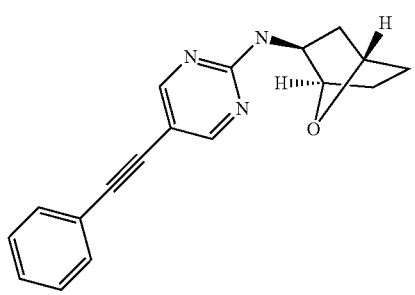 [SMILES: C(#Cc1cnc(N[C@H]2C[C@@H]3CC[C@H]2O3)nc1)c1ccccc1]

The title compound, MS: m/e=292.1 (M+H⁺), can be prepared in accordance with the general method of example 1, step 3 from 2-methanesulfonyl-5-phenylethynyl-pyrimidine (example 1, step 2) and rac-(7-oxa-bicyclo[2.2.1]hept-2-yl)amine (can be prepared in accordance with the literature described in the patent EP 1958666).

Example 5

Isomeric Mixture of (2,6-dimethoxy-cyclohexyl)-(5-phenylethynyl-pyrimidin-2-yl)-amine

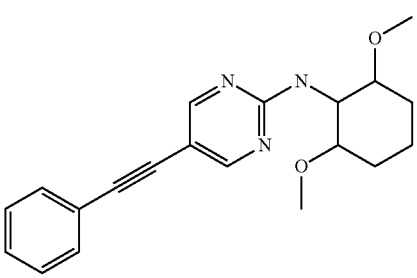 [SMILES: COC1CCCC(OC)C1Nc1ncc(C#Cc2ccccc2)cn1]

The title compound, MS: m/e=338.4 (M+H⁺), can be prepared in accordance with the general method of example 1, step 3 from 2-methanesulfonyl-5-phenylethynyl-pyrimidine (example 1, step 2) and an isomeric mixture of 2,6-dimethoxy-cyclohexylamine.

Example 6 trans-[4-(5-Phenylethynyl-pyrimidin-2-ylamino)-cyclohexyl]-methanol

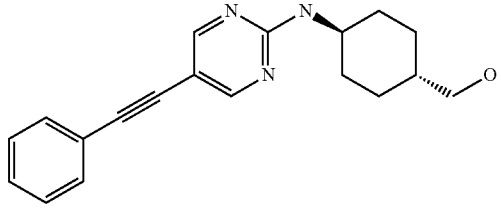 [SMILES: OC[C@H]1CC[C@H](Nc2ncc(C#Cc3ccccc3)cn2)CC1]

Step 1: trans-4-(5-Phenylethynyl-pyrimidin-2-ylamino)-cyclohexanecarboxylic acid methyl ester The title compound, MS: m/e=336.4 (M+H⁺), can be prepared in accordance with the general method of example 1, step 3 from 2-methanesulfonyl-5-phenylethynyl-pyrimidine (example 1, step 2) and trans-4-amino-cyclohexylcarboxylic acid methyl ester hydrochloride.

Step 2: trans-[4-(5-Phenylethynyl-pyrimidin-2-ylamino)-cyclohexyl]-methanol

To a suspension of LiAlH₄ (17 mg, 0.44 mmol) in 10 ml THF was added at 0-5° C. within 15 min a solution of trans-4-(5-phenylethynyl-pyrimidin-2-ylamino)-cyclohexanecarboxylic acid methyl ester (40 mg, 0.12 mmol) in 5 ml of THF. The reaction mixture was stirred for 30 min at 0-5° C. Saturated NaHCO₃ solution and brine were added to the reaction mixture which was extracted three times with dichloromethane. The combined organic phases were washed with brine, dried over Na₂SO₄ and filtered. The solvent was removed under reduced pressure and the crude product was purified by flash chromatography on silicagel (heptane:ethyl

Example 7 trans-4-(5-Phenylethynyl-pyrimidin-2-ylamino)-cyclohexanol

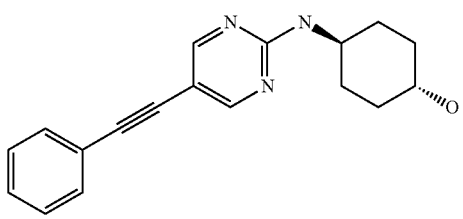

The title compound, MS: m/e=294.3 (M+H⁺), can be prepared in accordance with the general method of example 1, step 3 from 2-methanesulfonyl-5-phenylethynyl-pyrimidine (example 1, step 2) and trans-4-aminocyclohexanol hydrochloride.

Example 8 cis-4-(5-Phenylethynyl-pyrimidin-2-ylamino)-cyclohexanol

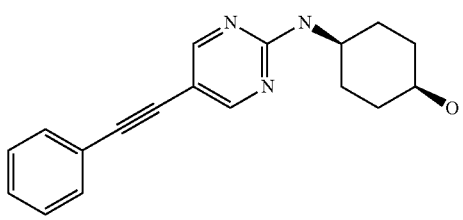 [SMILES: O[C@H]1CC[C@@H](Nc2ncc(C#Cc3ccccc3)cn2)CC1]

The title compound, MS: m/e=294.2 (M+H⁺), can be prepared in accordance with the general method of example 1, step 3 from 2-methanesulfonyl-5-phenylethynyl-pyrimidine (example 1, step 2) and cis-4-aminocyclohexanol hydrochloride.

Example 9 trans-(4-Methoxy-cyclohexyl)-(5-phenylethynyl-pyrimidin-2-yl)-amine

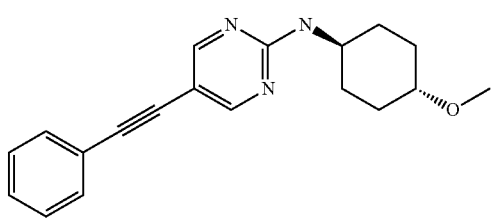 [SMILES: CO[C@H]1CC[C@H](Nc2ncc(C#Cc3ccccc3)cn2)CC1]

The title compound, MS: m/e=308.5 (M+H⁺), can be prepared in accordance with the general method of example 1, step 3 from 2-methanesulfonyl-5-phenylethynyl-pyrimidine (example 1, step 2) and trans-4-methoxycyclohexanamine hydrochloride.

Example 10

Cis and Trans Mixture of 2-(5-phenylethynyl-pyrimidin-2-ylamino)-cyclohexanol

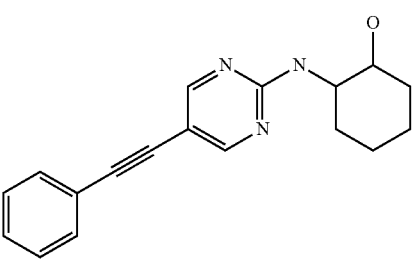 [SMILES: OC1CCCCC1Nc1ncc(C#Cc2ccccc2)cn1]

The title compound, MS: m/e=294.3 (M+H⁺), can be prepared in accordance with the general method of example 1, step 3 from 2-methanesulfonyl-5-phenylethynyl-pyrimidine (example 1, step 2) and a cis and trans mixture of 2-aminocyclohexanol.

Example 11

Cis and Trans Mixture of 3-(5-phenylethynyl-pyrimidin-2-ylamino)-cyclopentanol

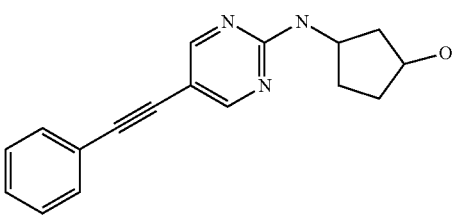 [SMILES: OC1CCC(Nc2ncc(C#Cc3ccccc3)cn2)C1]

The title compound, MS: m/e=280.3 (M+H⁺), can be prepared in accordance with the general method of example 1, step 3 from 2-methanesulfonyl-5-phenylethynyl-pyrimidine (example 1, step 2) and a cis and trans mixture of 3-aminocyclopentanol.

Example 12

Cis and Trans Mixture of 2-(5-phenylethynyl-pyrimidin-2-ylamino)-cyclopentanol

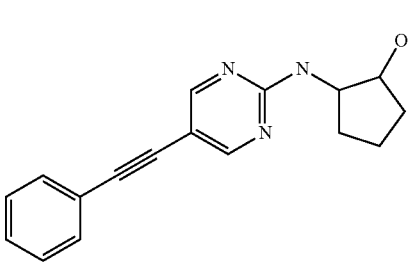 [SMILES: OC1CCCC1Nc1ncc(C#Cc2ccccc2)cn1]

The title compound, MS: m/e=280.3 (M+H⁺), can be prepared in accordance with the general method of example 1, step 3 from 2-methanesulfonyl-5-phenylethynyl-pyrimidine (example 1, step 2) and a cis and trans mixture of 2-aminocyclopentanol.

Example 13

Cyclopentyl-(5-phenylethynyl-pyridin-2-yl)-amine

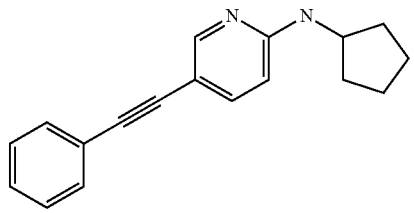 [SMILES: C(#Cc1ccc(NC2CCCC2)nc1)c1ccccc1]

Step 1: 5-Phenylethynyl-pyridin-2-ylamine

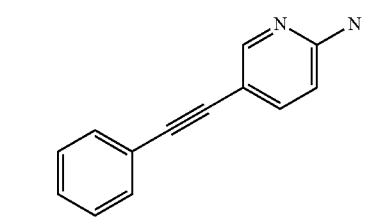 [SMILES: Nc1ccc(C#Cc2ccccc2)cn1]

Bis-(triphenylphosphine)-palladium(II)dichloride (320 mg, 0.45 mmol) was dissolved in 50 ml THF and 2-amino-5-iodopyrdine (2.0 g, 9.1 mmol) and phenylacetylene (2.0 ml, 18.2 mmol) were added at room temperature. Et₃N (3.8 ml, 27 3 mmol), triphenylphosphine (72 mg, 0.27 mmol) and copper (I)iodide (52 mg, 0.27 mmol) were added and the mixture was stirred for 2 hours at 65° C. The reaction mixture was cooled and extracted once with saturated NaHCO₃ solution and three times with ethyl acetate. The organic layers were combined, dried with sodium sulfate, filtered and evaporated to dryness. The crude product was suspended in 5 ml of dichloromethane, stirred for 15 minutes and filtered. The crystals were washed with a small volume of dichloromethane and dried for 1 hour at 50° C. and <20 mbar. The desired compound was obtained as a light yellow solid (1.1 g, 63%), MS: m/e=195.3 (M+H⁺).

Step 2: Cyclopentyl-(5-phenylethynyl-pyridin-2-yl)-amine

5-Phenylethynyl-pyridin-2-ylamine (100 mg, 0.515 mmol), cyclopentanone (77 mg, 0.927 mmol) and 2-picoline borane (85 mg, 0.927 mmol) were dissolved in 5.5 ml MeOH:AcOH (10:1 v/v) and stirred for 48 hours at 40° C. MeOH was then evaporated and the residue was acidified to pH 1 with 6 ml 10% HCl. The resulting white suspension was stirred for 2 hours. The mixture was extracted with dichloromethane and brine. The pH of the aqueous layer was adjusted to 12 by addition of conc. NaOH and the mixture was extracted twice with dichloromethane. The organic extracts were dried with sodium sulfate, filtered and evaporated. The crude product was purified by flash chromatography on silicagel (heptane/ethyl acetate 100:0→50:50 gradient). The desired compound was obtained as a light yellow solid (70 mg, 53%), MS: m/e=263.3 (M+H⁺).

Example 14

(5-Phenylethynyl-pyridin-2-yl)-(tetrahydro-pyran-4-yl)-amine

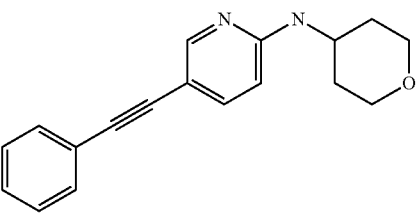 [SMILES: C(#Cc1ccc(NC2CCOCC2)nc1)c1ccccc1]

The title compound, MS: m/e=279.3 (M+H⁺), can be prepared in accordance with the general method of example 13, step 2 from 5-phenylethynyl-pyridin-2-ylamine (example 13, step 1) and tetrahydro-4H-pyran-4-one.

Example 15

Cyclohexyl-(5-phenylethynyl-pyrimidin-2-yl)-amine

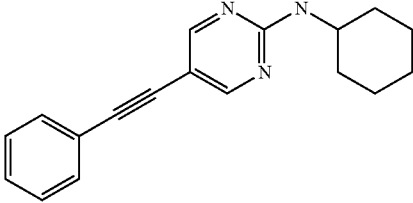 [SMILES: C(#Cc1cnc(NC2CCCCC2)nc1)c1ccccc1]

The title compound, white solid, MS: m/e=278.2 (M+H⁺), can be prepared in accordance with the general method of example 1, step 3 from 2-methanesulfonyl-5-phenylethynyl-pyrimidine (example 1, step 2) and cyclohexanamine.

Example 16

2,2-Dimethyl-4-(5-phenylethynyl-pyrimidin-2-ylamino)-cyclohexanol

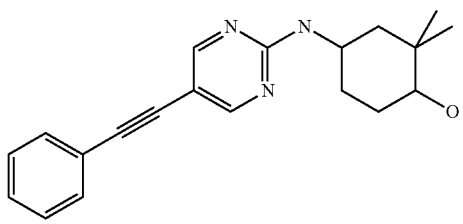 [SMILES: CC1(C)CC(Nc2ncc(C#Cc3ccccc3)cn2)CCC1O]

Step 1: 4-Hydroxy-3,3-dimethyl-cyclohexanone

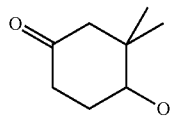

The title compound can be prepared according to example 7 in the literature *Journal of Medicinal Chemistry*, 2006, Vol. 49, No. 11.

Step 2: 4-Benzylamino-2,2-dimethyl-cyclohexanol

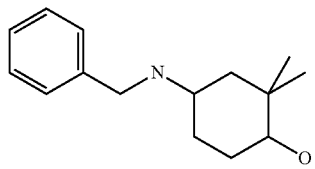 [SMILES: CC1(C)CC(NCc2ccccc2)CCC1O]

(0.43 g, 3 0 mmol) 4-Hydroxy-3,3-dimethylcyclohexanone (example 16, step 1) was dissolved in dichloromethane (15 ml) and the mixture was cooled to 0-5° C. Sodium triacetoxyborohydride (640 mg, 3.0 mmol, 1.0 equiv.), benzylamine (400 µl, 3.63 mmol, 1.2 equiv.) and acetic acid (173 µl, 3.0 mmol, 1.0 equiv.) were added at 0° C. The mixture was stirred for 3 hours at 0-5° C.

The reaction mixture was treated with sat. NaHCO$_3$ solution and extracted twice with a small volume of CH$_2$Cl$_2$. The organic layers were loaded directly to silica gel column and the crude material was purified by flash chromatography on silica gel (20 gr, methanol/dichloromethane gradient, 0:100 to 10:90). The desired diast. rac 4-benzylamino-2,2-dimethyl-cyclohexanol (420 mg, 60% yield) was obtained as a colorless semi solid, MS: m/e=234.2 (M+H$^+$).

Step 3: 4-Amino-2,2-dimethyl-cyclohexanol

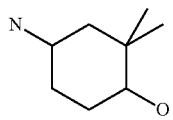

The title compound, a colorless oil, MS: m/e=144.1 (M+H+), can be prepared from 4-benzylamino-2,2-dimethyl-cyclohexanol (example 16, step 2) by hydrogenation 16 hours at room temperature using Pd/C (10%) in ethylacetate.

Step 4: 2,2-Dimethyl-4-(5-phenylethynyl-pyrimidin-2-ylamino)-cyclohexanol

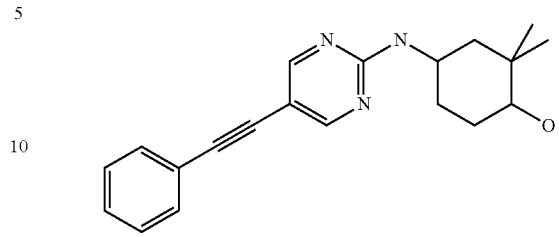

The title compound, yellow solid, MS: m/e=322.2 (M+H$^+$), can be prepared in accordance with the general method of example 1, step 3 from 2-methanesulfonyl-5-phenylethynyl-pyrimidine (example 1, step 2) and diast. rac 4-amino-2,2-dimethyl-cyclohexanol (example 16, step 3).

Example 17

(1S,4S or 1R,4R)-2,2-Dimethyl-4-(5-phenylethynyl-pyrimidin-2-ylamino)-cyclohexanol

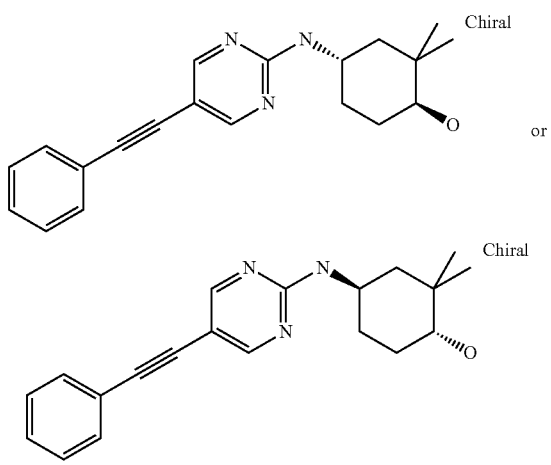

The title compound, white solid, MS: m/e=322.2 (M+H$^+$), can be prepared by separation of 2,2-diast. rac dimethyl-4-(5-phenylethynyl-pyrimidin-2-ylamino)-cyclohexanol (example 16) using a chiral column (chiralpak AD with heptane: isopropanol 80:20 as solvent).

Example 18 trans-4-(3-Fluoro-5-phenylethynyl-pyridin-2-ylamino)-cyclohexanol

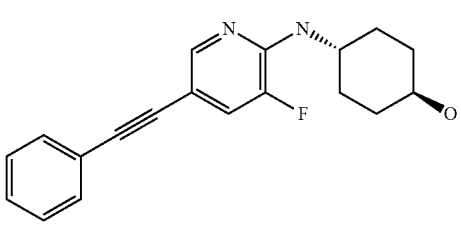 [SMILES: O[C@H]1CC[C@H](Nc2ncc(C#Cc3ccccc3)cc2F)CC1]

Step 1: trans-4-(3-Fluoro-5-iodo-pyridin-2-ylamino)-cyclohexanol

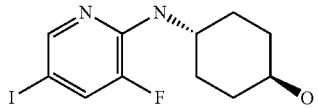 [SMILES: O[C@H]1CC[C@H](Nc2ncc(I)cc2F)CC1]

2,3-Difluoro-5-iodopyridine (300 mg, 1.24 mmol) was dissolved in dioxane (3 ml) and trans-4-aminocyclohexanol hydrochloride (227 mg, 1.49 mmol, 1.2 equiv.) and $Cs_2CO_3$ (1.01 g, 3.11 mmol, 2.5 equiv.) were added at room temperature. The mixture was stirred for 3 hours at 100° C. The reaction mixture was evaporated and treated with sat. $NaHCO_3$ solution and extracted twice with a small volume of $CH_2Cl_2$. The organic layers were loaded directly to silica gel column and the crude material was purified by flash chromatography on silica gel (20 gr, ethyl acetate/heptane gradient, 0:100 to 0:100). The desired trans-4-(3-fluoro-5-iodopyridin-2-ylamino)cyclohexanol (65 mg, 16% yield) was obtained as a white solid, MS: m/e=337.1 (M+H$^+$).

Step 2: trans-4-(3-Fluoro-5-phenylethynyl-pyridin-2-ylamino)-cyclohexanol

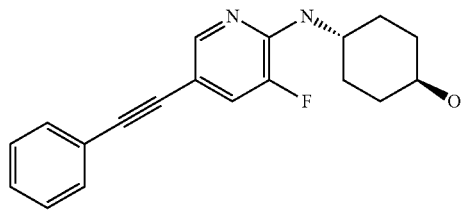 [SMILES: O[C@H]1CC[C@H](Nc2ncc(C#Cc3ccccc3)cc2F)CC1]

The title compound, yellow solid, MS: m/e=311.2 (M+H$^+$), can be prepared in accordance with the general method of example 1, step 1 from trans-4-(3-fluoro-5-iodopyridin-2-ylamino)cyclohexanol (example 18, step 1) and phenylacetylene.

Example 19 trans-(4-Methyl-cyclohexyl)-(5-phenylethynyl-pyrimidin-2-yl)-amine

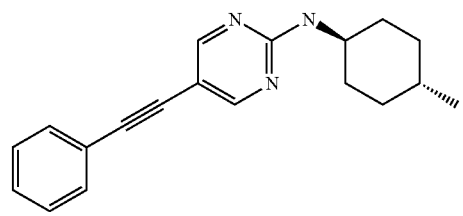 [SMILES: C[C@H]1CC[C@H](Nc2ncc(C#Cc3ccccc3)cn2)CC1]

The title compound, white solid, MS: m/e=292.2 (M+H$^+$), can be prepared in accordance with the general method of example 1, step 3 from 2-methanesulfonyl-5-phenylethynyl-pyrimidine (example 1, step 2) and 4-methyl-cyclohexylamine.

Example 20

(5-Phenylethynyl-pyrimidin-2-yl)-(tetrahydro-pyran-4-ylmethyl)-amine

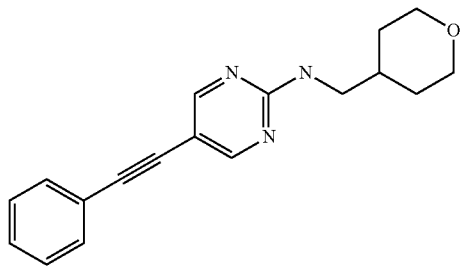 [SMILES: C(#Cc1cnc(NCC2CCOCC2)nc1)c1ccccc1]

The title compound, white solid, MS: m/e=294.2 (M+H$^+$), can be prepared in accordance with the general method of example 1, step 3 from 2-methanesulfonyl-5-phenylethynyl-pyrimidine (example 1, step 2) and (tetrahydro-2H-pyran-4-yl)methanamine.

Example 21

(3-Methyl-oxetan-3-ylmethyl)-(5-phenylethynyl-pyrimidin-2-yl)-amine

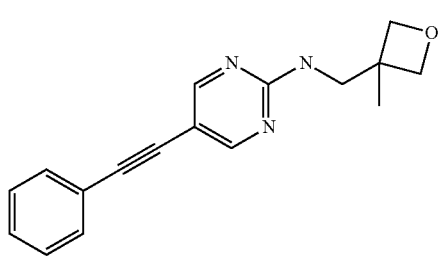 [SMILES: CC1(CNc2ncc(C#Cc3ccccc3)cn2)COC1]

The title compound, white solid, MS: m/e=280.2 (M+H$^+$), can be prepared in accordance with the general method of example 1, step 3 from 2-methanesulfonyl-5-phenylethynyl-pyrimidine (example 1, step 2) and (3-methyloxetan-3-yl)methanamine.

Example 22 rac-4-(5-Phenylethynyl-pyrimidin-2-yloxy)-cyclohexanol

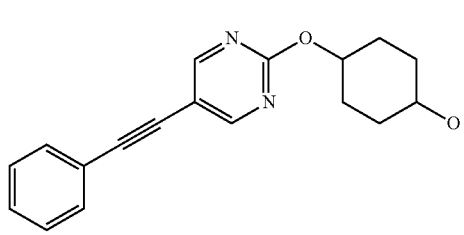 [SMILES: OC1CCC(Oc2ncc(C#Cc3ccccc3)cn2)CC1]

Example 23 trans-4-(5-Phenylethynyl-pyrimidin-2-yloxy)-cyclohexanol

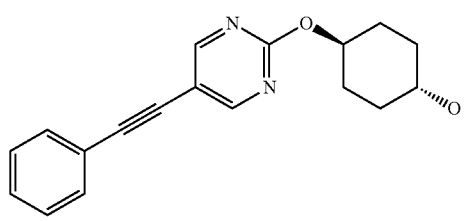

The title compound, yellow solid, MS: m/e=295.1 (M+H$^+$), can be prepared by separation of rac-4-(5-phenylethynyl-pyrimidin-2-yloxy)-cyclohexanol (example 22) using a chiral column (chiralpak AD with heptane:isopropanol 82:18 as solvent).

Example 24

2-(3-Methyl-oxetan-3-ylmethoxy)-5-phenylethynyl-pyrimidine

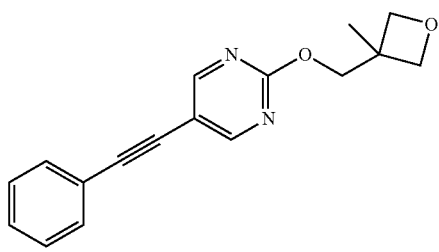 [SMILES: CC1(COc2ncc(C#Cc3ccccc3)cn2)COC1]

The title compound, yellow solid, MS: m/e=281.1 (M+H$^+$), can be prepared in accordance with the general method of example 1, step 3 from 2-methanesulfonyl-5-phenylethynyl-pyrimidine (example 1, step 2) and (3-methyl-oxetan-3-yl)-methanol by using Cs$_2$CO$_3$ as base and dioxane as solvent for 16 hours at 100° C.

Example 25 trans-3-(5-Phenylethynyl-pyrimidin-2-yloxymethyl)-cyclobutanol

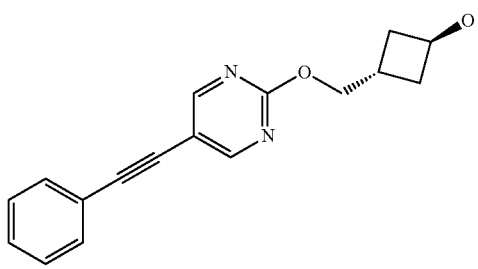 [SMILES: O[C@H]1C[C@H](COc2ncc(C#Cc3ccccc3)cn2)C1]

The title compound, yellow solid, MS: m/e=295.3 (M+H$^+$), can be prepared in accordance with the general method of example 1, step 3 from 2-methanesulfonyl-5-phenylethynyl-pyrimidine (example 1, step 2) and cyclohexane-1,4-diol by using Cs$_2$CO$_3$ as base and dioxane as solvent for 16 hours at 100° C.

The title compound, yellow solid, MS: m/e=281.1 (M+H$^+$), can be prepared in accordance with the general method of example 1, step 3 from 2-methanesulfonyl-5-phenylethynyl-pyrimidine (example 1, step 2) and 3-(hydroxymethyl)cyclobutanol by using Cs$_2$CO$_3$ as base and dioxane as solvent for 16 hours at 100° C. and by separation of the received isomers-mixture using a chiral column (Lux2 Cellulose with heptane:isopropanol 85:15 as solvent).

Example 26 trans-[3-(5-Phenylethynyl-pyrimidin-2-yloxy)-cyclobutyl]-methanol

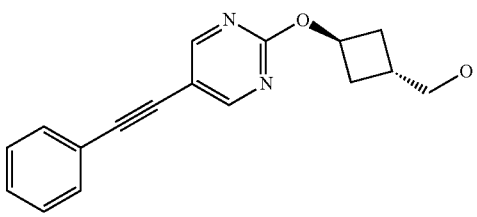 [SMILES: OC[C@H]1C[C@H](Oc2ncc(C#Cc3ccccc3)cn2)C1]

The title compound, yellow solid, MS: m/e=281.1 (M+H$^+$), can be prepared in accordance with the general method of example 1, step 3 from 2-methanesulfonyl-5-phenylethynyl-pyrimidine (example 1, step 2) and 3-(hydroxymethyl)cyclobutanol by using Cs$_2$CO$_3$ as base and dioxane as solvent for 16 hours at 100° C. and by separation of the received isomers-mixture using a chiral column (Lux2 Cellulose with heptane:isopropanol 85:15 as solvent).

Example 27 rac-4-(3-Fluoro-5-phenylethynyl-pyridin-2-yloxy)-cyclohexanol

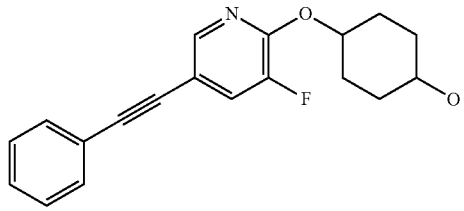 [SMILES: OC1CCC(Oc2ncc(C#Cc3ccccc3)cc2F)CC1]

The title compound, yellow oil, MS: m/e=312.1 (M+H$^+$), can be prepared in accordance with the general method of example 18 from 2,3-difluoro-5-iodopyridine, cyclohexane-1,4-diol and phenylacetylene.

Example 28

2-Cyclohexyloxy-5-phenylethynyl-pyridine

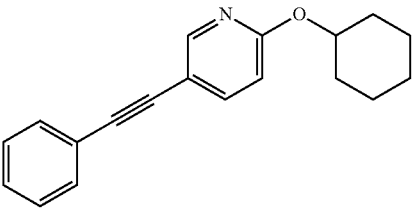 [SMILES: C(#Cc1ccc(OC2CCCCC2)nc1)c1ccccc1]

The title compound, brown oil, MS: m/e=278.1 (M+H$^+$), can be prepared in accordance with the general method of example 18, step 2 from 2-(cyclohexyloxy)-5-iodopyridine and phenylacetylene.

Example 29

3-Fluoro-2-(3-methyl-oxetan-3-ylmethoxy)-5-phenylethynyl-pyridine

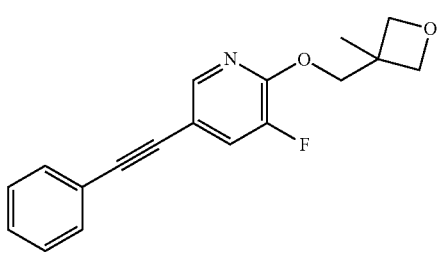 [SMILES: CC1(COc2ncc(C#Cc3ccccc3)cc2F)COC1]

The title compound, yellow solid, MS: m/e=298.3 (M+H$^+$), can be prepared in accordance with the general method of example 18 from 2,3-difluoro-5-iodopyridine, (3-methyloxetan-3-yl)methanol and phenylacetylene.

Example 30

4-(5-Phenylethynyl-pyridin-2-ylmethyl)-morpholin-3-one

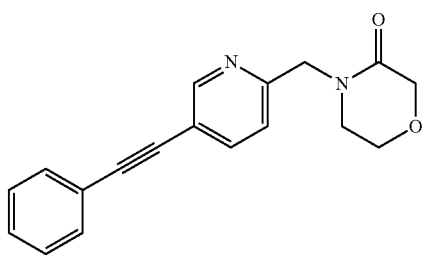 [SMILES: O=C1COCCN1Cc1ccc(C#Cc2ccccc2)cn1]

Step 1: (5-Phenylethynyl-pyridin-2-yl)-methanol

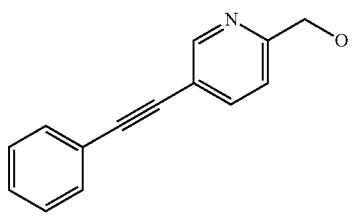 [SMILES: OCc1ccc(C#Cc2ccccc2)cn1]

The title compound, light brown solid, MS: m/e=210.2 (M+H$^+$), can be prepared in accordance with the general method of example 1, step 1 from (5-bromopyridin-2-yl)methanol and phenylacetylene.

Step 2: 4-(5-Phenylethynyl-pyridin-2-ylmethyl)-morpholin-3-one (0.20 g, 0.96 mmol) (5-Phenylethynyl-pyridin-2-yl)-methanol (example 31, step 1) was dissolved in dichloromethane (5 ml) and methanesulfonyl chloride (75 µl, 0.96 mmol, 1.0 equiv.) and triethylamine (270 µl, 1.91 mmol, 2 equiv.) were added at 0-5° C. The mixture was stirred for 1 hour at room temperature. The reaction mixture was evaporated, dissolved in 2 ml DMF and added to a suspension of morpholin-3-one (97 mg, 0.96 mmol, 1.0 equiv.) previously treated with sodium hydride (60%) (69 mg, 1.43 mmol, 1.5 equiv.) in 2 ml DMF. The mixture was stirred for 3 hours at room temperature. The reaction mixture was treated with sat. NaHCO$_3$ solution and extracted twice with EtOAc. The organic layers were extracted with water, dried over sodium sulfate and evaporated to dryness. The crude material was purified by flash chromatography on silica gel (20 gr, ethyl acetate/heptane gradient, 0:100 to 0:100). The desired 4-(5-phenylethynyl-pyridin-2-ylmethyl)-morpholin-3-one (150 mg, 54% yield) was obtained as a light brown solid, MS: m/e=293.1 (M+H$^+$).

Example 31

3-(5-Phenylethynyl-pyridin-2-ylmethyl)-oxazolidin-2-one

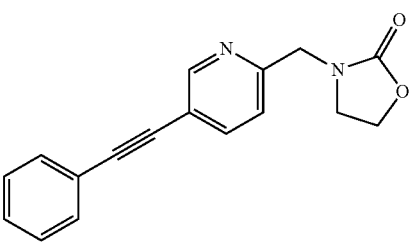 [SMILES: O=C1OCCN1Cc1ccc(C#Cc2ccccc2)cn1]

The title compound, white solid, MS: m/e=279.2 (M+H$^+$), can be prepared in accordance with the general method of example 31, step 2 from (5-phenylethynyl-pyridin-2-yl)-methanol (example 31, step 1) and oxazolidin-2-one.

Example 32

1-(5-Phenylethynyl-pyridin-2-ylmethyl)-piperidin-2-one

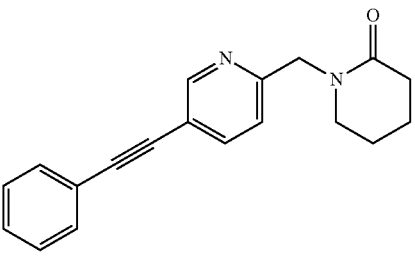 [SMILES: O=C1CCCCN1Cc1ccc(C#Cc2ccccc2)cn1]

The title compound, brown oil, MS: m/e=291.2 (M+H$^+$), can be prepared in accordance with the general method of example 31, step 2 from (5-phenylethynyl-pyridin-2-yl)-methanol (example 31, step 1) and piperidin-2-one.

Example 33

4,4-Dimethyl-1-(5-phenylethynyl-pyridin-2-ylmethyl)-pyrrolidin-2-one

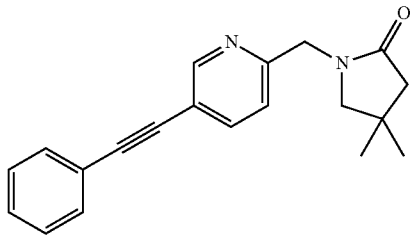 [SMILES: CC1(C)CC(=O)N(Cc2ccc(C#Cc3ccccc3)cn2)C1]

The title compound, light brown oil, MS: m/e=305.2 (M+H$^+$), can be prepared in accordance with the general method of example 31, step 2 from (5-phenylethynyl-pyridin-2-yl)-methanol (example 31, step 1) and 4,4-dimethyl-pyrrolidin-2-one.

Example 34

3-(5-Phenylethynyl-pyridin-2-ylmethyl)-[1,3]oxazinan-2-one

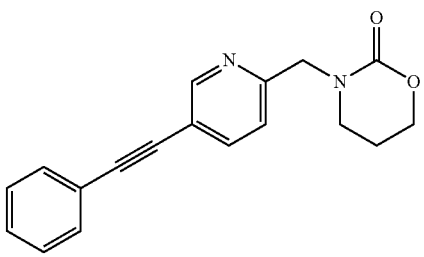 [SMILES: O=C1OCCCN1Cc1ccc(C#Cc2ccccc2)cn1]

The title compound, light brown solid, MS: m/e=293.1 (M+H$^+$), can be prepared in accordance with the general method of example 31, step 2 from (5-phenylethynyl-pyridin-2-yl)-methanol (example 31, step 1) and 1,3-oxazinan-2-one.

Example 35

1-Methyl-3-(5-phenylethynyl-pyridin-2-ylmethyl)-imidazolidin-2-one

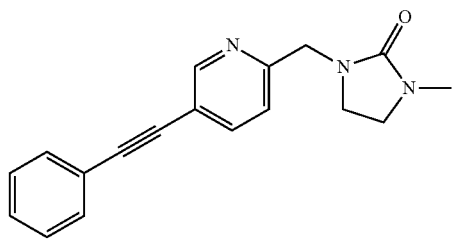 [SMILES: CN1CCN(Cc2ccc(C#Cc3ccccc3)cn2)C1=O]

The title compound, light brown solid, MS: m/e=293.1 (M+H$^+$), can be prepared in accordance with the general method of example 31, step 2 from (5-phenylethynyl-pyridin-2-yl)-methanol (example 31, step 1) and 1-methyl-imidazolidin-2-one.

Example 36

5,5-Dimethyl-1-(5-phenylethynyl-pyridin-2-ylmethyl)-pyrrolidin-2-one

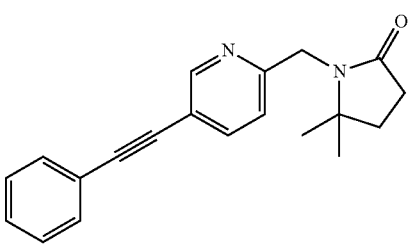 [SMILES: CC1(C)CCC(=O)N1Cc1ccc(C#Cc2ccccc2)cn1]

The title compound, light yellow oil, MS: m/e=305.2 (M+H$^+$), can be prepared in accordance with the general method of example 31, step 2 from (5-phenylethynyl-pyridin-2-yl)-methanol (example 31, step 1) and 5,5-dimethyl-pyrrolidin-2-one.

Example 37

1-Phenyl-3-(5-phenylethynyl-pyridin-2-ylmethyl)-imidazolidin-2-one

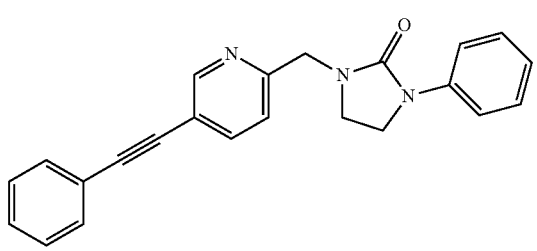 [SMILES: O=C1N(Cc2ccc(C#Cc3ccccc3)cn2)CCN1c1ccccc1]

The title compound, light yellow solid, MS: m/e=354.3 (M+H$^+$), can be prepared in accordance with the general method of example 31, step 2 from (5-phenylethynyl-pyridin-2-yl)-methanol (example 31, step 1) and 1-phenyl-imidazolidin-2-one.

Example 38

5,5-Dimethyl-1-(5-phenylethynyl-pyridin-2-ylmethyl)-piperidin-2-one

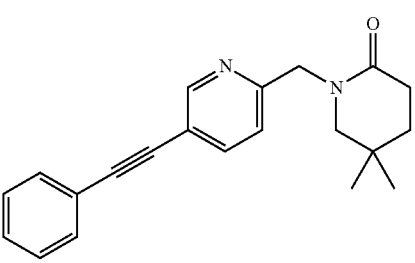 [SMILES: CC1(C)CCC(=O)N(Cc2ccc(C#Cc3ccccc3)cn2)C1]

The title compound, yellow oil, MS: m/e=319.2 (M+H⁺), can be prepared in accordance with the general method of example 31, step 2 from (5-phenylethynyl-pyridin-2-yl)-methanol (example 31, step 1) and 5,5-dimethyl-piperidin-2-one.

Example 39 rac-3-Methyl-1-(5-phenylethynyl-pyridin-2-ylmethyl)-pyrrolidin-2-one

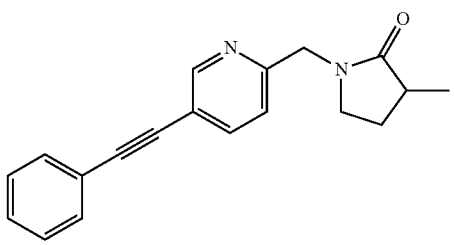 [SMILES: CC1CCN(Cc2ccc(C#Cc3ccccc3)cn2)C1=O]

The title compound, light yellow oil, MS: m/e=291.1 (M+H⁺), can be prepared in accordance with the general method of example 31, step 2 from (5-phenylethynyl-pyridin-2-yl)-methanol (example 31, step 1) and rac-3-methyl-pyrrolidin-2-one.

Example 40

1-Methyl-3-(5-phenylethynyl-pyridin-2-ylmethyl)-tetrahydro-pyrimidin-2-one

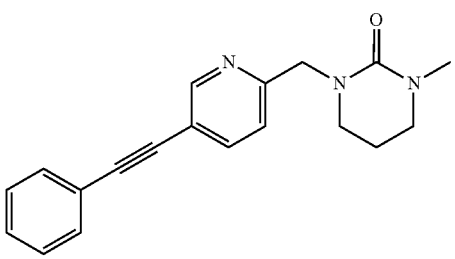 [SMILES: CN1CCCN(Cc2ccc(C#Cc3ccccc3)cn2)C1=O]

The title compound, light yellow oil, MS: m/e=306.2 (M+H⁺), can be prepared in accordance with the general method of example 31, step 2 from (5-phenylethynyl-pyridin-2-yl)-methanol (example 31, step 1) and 1-methyl-tetrahydro-pyrimidin-2-one.

Example 41 rac-3-[1-(5-Phenylethynyl-pyridin-2-yl)-ethyl]-oxazolidin-2-one

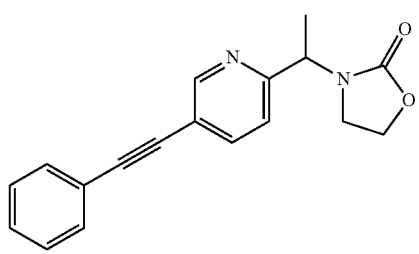 [SMILES: CC(c1ccc(C#Cc2ccccc2)cn1)N1CCOC1=O]

Step 1: rac-1-(5-Phenylethynyl-pyridin-2-yl)-ethanol

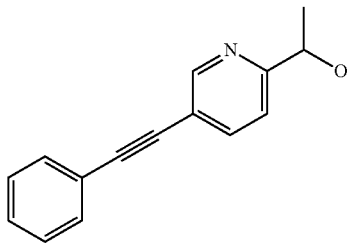 [SMILES: CC(O)c1ccc(C#Cc2ccccc2)cn1]

The title compound, brown solid, MS: m/e=224.2 (M+H⁺), can be prepared in accordance with the general method of example 31, step 1 from rac-1-(5-bromopyridin-2-yl)ethanol and phenylacetylene.

Step 2: rac-3-[1-(5-Phenylethynyl-pyridin-2-yl)-ethyl]-oxazolidin-2-one

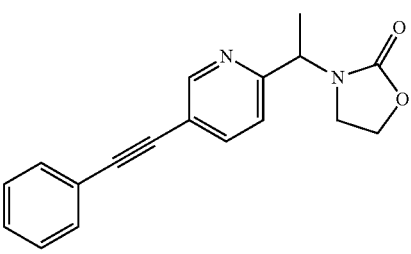 [SMILES: CC(c1ccc(C#Cc2ccccc2)cn1)N1CCOC1=O]

The title compound, white solid, MS: m/e=293.1 (M+H⁺), can be prepared in accordance with the general method of example 31, step 2 from rac-1-(5-phenylethynyl-pyridin-2-yl)-ethanol (example 42, step 1) and oxazolidin-2-one.

Example 42

3-(5-Phenylethynyl-pyrimidin-2-ylmethyl)-oxazolidin-2-one

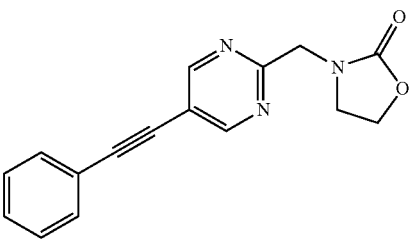

The title compound, white solid, MS: m/e=280.2 (M+H⁺), can be prepared in accordance with the general method of example 31, step 1 and step 2 from (5-bromo-pyrimidin-2-yl)-methanol (*Synlett* (2008), (4), 543-546), phenylacetylene and oxazolidin-2-one.

Example 43

Methyl-(5-phenylethynyl-pyrimidin-2-yl)-(tetrahydro-pyran-4-yl)-amine

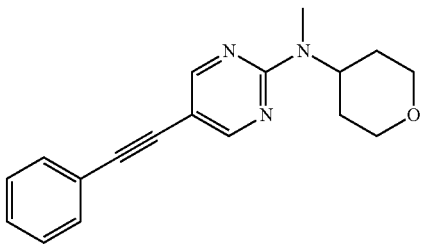 [SMILES: CN(c1ncc(C#Cc2ccccc2)cn1)C1CCOCC1]

(12 mg, 43 μmol) (5-Phenylethynyl-pyrimidin-2-yl)-(tetrahydro-pyran-4-yl)-amine (example 2) was dissolved in DMF (0.2 ml) and sodium hydride (60%) (2 mg, 52 μmol, 1.2 equiv.) was added at room temperature. The mixture was stirred for 30 min. at room temperature and iodomethane (3 μl, 52 μmol, 1.2 equiv.) was added. The mixture was stirred for 1 hour at 40° C.

The reaction mixture was treated with sat. NaHCO$_3$ solution and extracted twice with a small volume of CH$_2$Cl$_2$. The organic layers were loaded directly to silica gel column and the crude material was purified by flash chromatography on silica gel (20 gr, EtOAc/heptane gradient, 0:100 to 60:40). The desired methyl-(5-phenylethynyl-pyrimidin-2-yl)-(tetrahydro-pyran-4-yl)-amine (7.4 mg, 59% yield) was obtained as a colorless oil, MS: m/e=294.2 (M+H$^+$).

Example 44

3-(5-Phenylethynyl-pyridin-2-ylmethyl)-oxazolidin-2-one

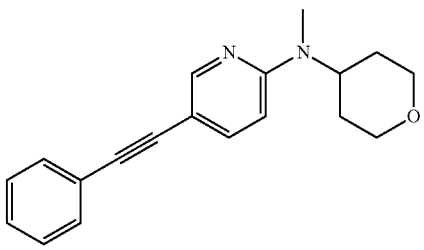 [SMILES: CN(c1ccc(C#Cc2ccccc2)cn1)C1CCOCC1]

The title compound, colorless oil, MS: m/e=293.2 (M+H$^+$), can be prepared in accordance with the general method of example 44 from (5-phenylethynyl-pyrimidin-2-yl)-(tetrahydro-pyran-4-yl)-amine (example 14).

The invention claimed is:
1. A compound of formula I

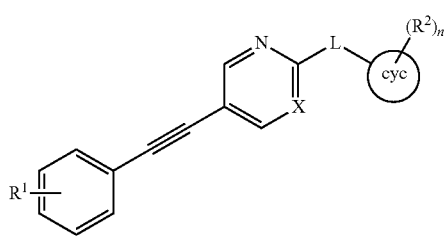

wherein
R$^1$ is hydrogen, halogen, lower alkyl or lower alkyl substituted by halogen;
R$^2$ is hydrogen, lower alkyl, =O, lower alkoxy, phenyl, hydroxy or lower alkyl substituted by hydroxy;
X is CF or CH;
L is —NR$^3$—, —NHC(R$^3$)$_2$—, —OC(R$^3$)$_2$—, or —CR$^4$R$^{4'}$—;
R$^3$ is hydrogen or lower alkyl;
R$^4$ and R$^{4'}$ are each independently hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof.

2. The compound of claim 1 having formula IA

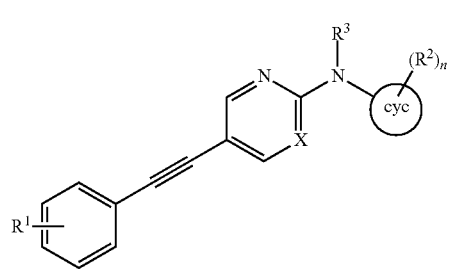

wherein
R$^1$ is hydrogen, halogen, lower alkyl or lower alkyl substituted by halogen;
R$^2$ is hydrogen, lower alkyl, =O, lower alkoxy, phenyl, hydroxy or lower alkyl substituted by hydroxy;
X is CF or CH;
R$^3$ is hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof.

3. The compound of claim 2, having formula IA-2,

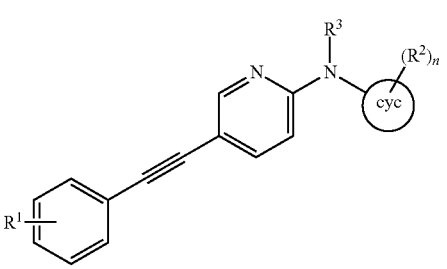

wherein
R$^1$ is hydrogen, halogen, lower alkyl or lower alkyl substituted by halogen;
R$^2$ is hydrogen, lower alkyl, =O, lower alkoxy, phenyl, hydroxy or lower alkyl substituted by hydroxy;
R$^3$ is hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and n is 1, 2 or 3;
or a pharmaceutically acceptable acid addition salt, racemic mixture, or stereoisomer thereof.

4. The compound of claim 3, selected from the group consisting of
cyclopentyl-(5-phenylethynyl-pyridin-2-yl)-amine and
(5-phenylethynyl-pyridin-2-yl)-(tetrahydro-pyran-4-yl)-amine.

5. The compound of claim 2, having formula IA-3

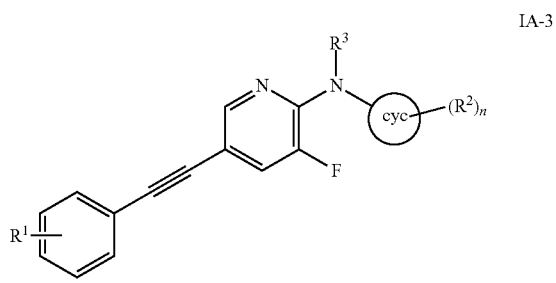

IA-3 wherein
$R^1$ is hydrogen, halogen, lower alkyl or lower alkyl substituted by halogen;
$R^2$ is hydrogen, lower alkyl, =O, lower alkoxy, phenyl, hydroxy or lower alkyl substituted by hydroxy;
$R^3$ is hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof.

6. The compound of claim 1, having formula IC

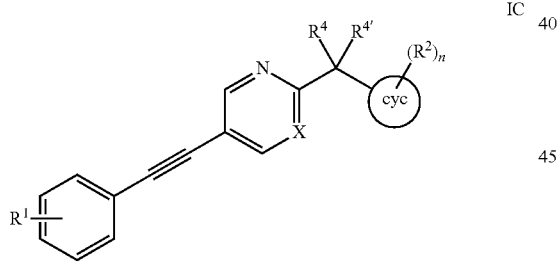

IC wherein
$R^1$ is hydrogen, halogen, lower alkyl or lower alkyl substituted by halogen;
$R^2$ is hydrogen, lower alkyl, =O, lower alkoxy, phenyl, hydroxy or lower alkyl substituted by hydroxy;
X is CF or CH;
$R^4$ and $R^{4'}$ are each independently hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof.

7. The compound of claim 6, selected from the group consisting of
3-(5-phenylethynyl-pyridin-2-ylmethyl)-oxazolidin-2-one;
1-methyl-3-(5-phenylethynyl-pyridin-2-ylmethyl)-imidazolidin-2-one;
5,5-dimethyl-1-(5-phenylethynyl-pyridin-2-ylmethyl)-pyrrolidin-2-one;
1-phenyl-3-(5-phenylethynyl-pyridin-2-ylmethyl)-imidazolidin-2-one; and
rac-3-[1-(5-phenylethynyl-pyridin-2-yl)-ethyl]-oxazolidin-2-one.

8. The compound of claim 7, which is 3-(5-phenylethynyl-pyridin-2-ylmethyl)-oxazolidin-2-one.

9. The compound of claim 1, having formula ID

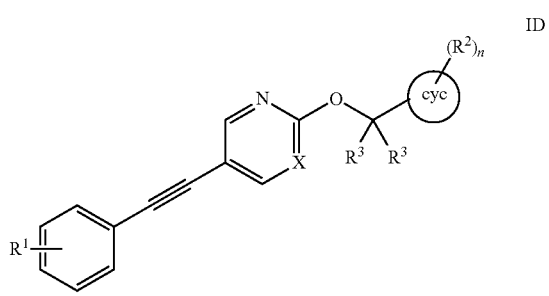

ID wherein
$R^1$ is hydrogen, halogen, lower alkyl or lower alkyl substituted by halogen;
$R^2$ is hydrogen, lower alkyl, =O, lower alkoxy, phenyl, hydroxy or lower alkyl substituted by hydroxy;
X is CF or CH;
$R^3$ is hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof.

10. The compound of claim 1, having formula IE

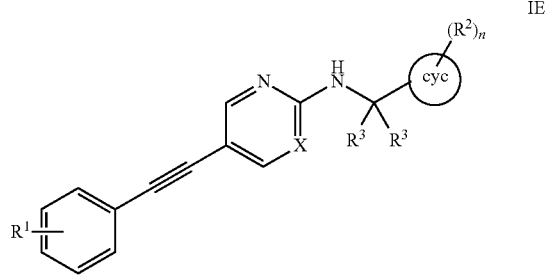

IE wherein
$R^1$ is hydrogen, halogen, lower alkyl or lower alkyl substituted by halogen;
$R^2$ is hydrogen, lower alkyl, =O, lower alkoxy, phenyl, hydroxy or lower alkyl substituted by hydroxy;
X is CF or CH;
$R^3$ is hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof.

11. The compound of claim 1, having formula IF

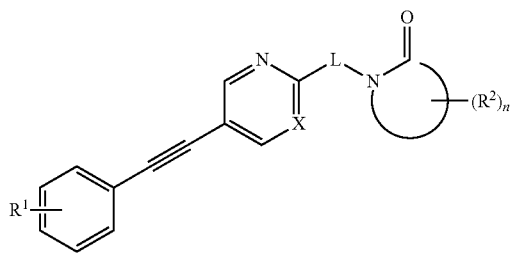

wherein
R¹ is hydrogen, halogen, lower alkyl or lower alkyl substituted by halogen;
R² is hydrogen, lower alkyl, =O, lower alkoxy, phenyl, hydroxy or lower alkyl substituted by hydroxy;
X is CF or CH;
L is —NR³—, —NHC(R³)₂—, —OC(R³)₂—, or —CR⁴R⁴'—;

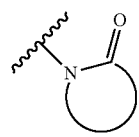 [SMILES: *NC=O]

is a 5 or 6 membered heterocycloalkyl, selected from the group consisting of morpholin-3-one, oxazolidin-2-one, pyrrolidin-2-one, piperidin-2-one, [1,3]oxazinan-2-one, imidazolin-2-one and tetrahydropyrimidin-2-one; and
n is 1, 2 or 3;
or a pharmaceutically acceptable acid addition salt, racemic mixture, or stereoisomer thereof.

12. The compound of claim 11, selected from the group consisting of
4-(5-phenylethynyl-pyridin-2-ylmethyl)-morpholin-3-one;
3-(5-phenylethynyl-pyridin-2-ylmethyl)-oxazolidin-2-one;
1-(5-phenylethynyl-pyridin-2-ylmethyl)-piperidin-2-one;
4,4-dimethyl-1-(5-phenylethynyl-pyridin-2-ylmethyl)-pyrrolidin-2-one;
3-(5-phenylethynyl-pyridin-2-ylmethyl)-[1,3]oxazinan-2-one; and
1-methyl-3-(5-phenylethynyl-pyridin-2-ylmethyl)-imidazolidin-2-one.

13. The compound of claim 11, selected from the group consisting of
5,5-dimethyl-1-(5-phenylethynyl-pyridin-2-ylmethyl)-pyrrolidin-2-one;
1-phenyl-3-(5-phenylethynyl-pyridin-2-ylmethyl)-imidazolidin-2-one;
5,5-dimethyl-1-(5-phenylethynyl-pyridin-2-ylmethyl)-piperidin-2-one,
rac-3-methyl-1-(5-phenylethynyl-pyridin-2-ylmethyl)-pyrrolidin-2-one;
1-methyl-3-(5-phenylethynyl-pyridin-2-ylmethyl)-tetrahydro-pyrimidin-2-one; and
rac-3-[1-(5-phenylethynyl-pyridin-2-yl)-ethyl]-oxazolidin-2-one.

14. A pharmaceutical composition comprising a therapeutically effective amount of a compound of formula I

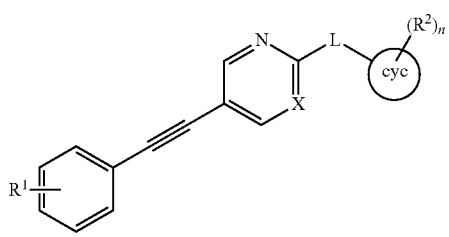

wherein
R¹ is hydrogen, halogen, lower alkyl or lower alkyl substituted by halogen;
R² is hydrogen, lower alkyl, =O, lower alkoxy, phenyl, hydroxy or lower alkyl substituted by hydroxy;
X is CF or CH;
L is —NR³—, —NHC(R³)₂—, —OC(R³)₂—, or —CR⁴R⁴';
R³ is hydrogen or lower alkyl;
R⁴ and R⁴' are each independently hydrogen or lower alkyl;
cyc is cycloalkyl or heterocycloalkyl, or is a non-aromatic bicycle selected from 7-oxa-bicyclo[2.2.1]hept-1-yl and bicyclo[2.2.1]hept-1-yl; and
n is 1, 2 or 3;
or a pharmaceutically acceptable acid addition salt, racemic mixture, or stereoisomer thereof
and a pharmaceutically acceptable carrier.

\* \* \* \* \*